United States Patent [19]
Anand et al.

[11] Patent Number: 5,939,255
[45] Date of Patent: Aug. 17, 1999

[54] YEAST ARTIFICIAL CHROMOSOMES CONTAINING DNA ENCODING THE CYSTIC FIBROSIS (CFTR) GENE

[75] Inventors: Rakesh Anand, Sandbach; Alexander Fred Markham, Crewe; John Craig Smith, Nr Knutsford; Rashida Anwar, Northwich; John Hamilton Riley, Nr Northwich; Donald James Ogilvie, Sale; Paul Elvin, Barnton, all of United Kingdom

[73] Assignee: Zeneca Limited, London, United Kingdom

[21] Appl. No.: 08/250,346

[22] Filed: May 27, 1994

Related U.S. Application Data

[63] Continuation of application No. 08/115,675, Sep. 2, 1993, abandoned, which is a continuation of application No. 07/879,117, May 4, 1992, abandoned, which is a continuation of application No. 07/578,616, Sep. 7, 1990, abandoned.

[30] Foreign Application Priority Data

Sep. 7, 1989 [GB] United Kingdom ............... 8920211

[51] Int. Cl.⁶ .............................. C12Q 1/68; C07H 17/00
[52] U.S. Cl. ............................................... 435/6; 536/23.5
[58] Field of Search ................... 536/23.1, 23.5; 435/172.1, 6; 935/22, 23

[56] References Cited

U.S. PATENT DOCUMENTS

| | | | |
|---|---|---|---|
| 4,959,317 | 9/1990 | Sauer | 435/172.3 |
| 5,240,846 | 8/1993 | Collins et al. | 435/240.1 |

FOREIGN PATENT DOCUMENTS

| | | |
|---|---|---|
| 0226288 | 6/1987 | European Pat. Off. . |
| A-0288299 | 10/1988 | European Pat. Off. . |
| A-0356021 | 2/1990 | European Pat. Off. . |

OTHER PUBLICATIONS

Goodfellow, *Nature*, 341: 102–103, 1989.
Roberts, *Science*, 240: 141–144, 1988.
Roberts, *Science*, 240: 282–285, 1988.
Koshland, *Science*, 245: 1029, 1989.
Marx, *Science*, 245: 923–925, 1989.
Rommens et al., *Science*, 245: 1059–1065, 1989.
Riordan et al., *Science*, 245: 1066–1073, 1989.
Kerem et al., *Science*, 245: 1073–1080, 1989.
Rommens et al., *Am. J. Hum. Genet.*, 43: 645–663, 1988.
Ramsay et al., *Genomics*, 6: 39–47, 1990.
Ianuzzi et al., *Am. J. Hum. Genet.*, 44: 695–703, 1989.
Estivill et al., *Genomics*, 1: 257–263, 1987.
Estivill et al., *Nature*, 326: 840–845, 1987.
Collins, Annual Meeting, 154th National American Association for the Advancement of Science, Abstract 25–3, 1988.
Collins et al., *Science*, 235: 1046–1049, 1987.
Lap–Chee Tsui, *Am. J. Hum. Genet.*, 44: 303–306, 1989.
Farrall et al., *Am. J. Hum. Genet.*, 43: 471–475, 1988.
Drumm et al., *Genomics*, 2: 346–354, 1988.
Silverman et al., *P.N.A.S., USA*, 86: 7485–7489, 1989.
Anand et al., *Nucleic Acids Research*, 17: 3425–3433, 1989.
Dean et al., *Genomics*, 3: 93–99, 1988.
Winter et al., *J. Clin. Chem. Biochem.*, 27(3): 129, 1989.
Schwartz et al. Cell 37:67 (1984).
Estivill et al. Am. J. Hum. Gen. 44:704 (1989).
McCormick et al. P.N.A.S. 86:9991 (1989).
Eliceiri et al P.N.A.S. 88:2179 (1991).
Pavan et al. P.N.A.S. 87:1300 (1990).
Traver et al. P.N.A.S. 86:5878 (1989).
Burke et al. Science 236:806 (1987).

*Primary Examiner*—Karen Cochrane Carlson
*Attorney, Agent, or Firm*—Cushman Darby & Cushman Intellectual Property Group of Pillsbury Madison & Sutro, LLP

[57] ABSTRACT

Yeast Artificial Chromosomes (YACS) containing DNA encoding the cystic fibrosis (CFTR) gene are described. The YACs allow detailed analysis of the coding and non-coding regions of the gene and the determination of cystic fibrosis alleles in sample DNA from an individual or individuals.

7 Claims, 5 Drawing Sheets

30 CYCLES

35 CYCLES 1 2 3 4

1 2 3 4

YEAST ARTIFICIAL CHROMOSOMES CONTAINING DNA ENCODING THE CYSTIC FIBROSIS (CFTR) GENE

CROSS-REFERENCES TO RELATED APPLICATIONS

The present application is a continuation of U.S. patent application Ser. No. 08/115,675, filed Sep. 2, 1993, now abandoned, which itself was a continuation of U.S. patent application Ser. No. 07/879,117, filed May 4, 1992, now abandoned, which itself was a continuation of U.S. patent application Ser. No. 07/578,616, filed Sep. 7, 1990, now abandoned.

BACKGROUND OF THE INVENTION

1. Field of the Invention

The present invention relates to nucleotide sequences and their use in methods for the detection, diagnosis and therapy of genetically inherited disorders. In particular the nucleotide sequences of the invention may be used for the detection of cystic fibrosis alleles. The invention also relates to nucleotide sequences coding for inherited disease associated genes such as cystic fibrosis and to RNA, such as mRNA, and polypeptides such as proteins, derived therefrom. Diagnostic kits are also provided for use in the diagnostic methods of the present invention.

2. Description of the Related Art

Available methods for the detection of cystic fibrosis are based on linkage studies. In general these comprise the use of labelled probes to detect restriction fragment length polymorphisms in sample genomic DNA. The distinguishing power of the genetic loci detected by the probes mentioned above is limited by the observed degree of polymorphism at such loci. Such probes may therefore identify the same restriction fragment for many individuals and the ability to distinguish between normal and cystic fibrosis alleles in such individuals is no longer possible. A need therefore exists for further and more informative methods of detection and diagnosis.

Cystic fibrosis (CF) is the most common lethal autosomal recessive disease in the Western world with a carrier frequency of ~1/20 and an incidence of 1/1600 live births. The disease is extremely rare in African and Asian populations, although cases have been reported in Japan. Affected patients exhibit elevated sodium chloride secretion in sweat and suffer from a variety of symptoms including bronchiectasis, respiratory failure and pancreatic insufficiency. The nature of the defect causing CF is unknown although it has been shown that sweat gland cells and respiratory epithelial cells from affected patients show a diminished permeability to chloride ions and a defective response to beta adrenergic agents (M J Stutts et al, 1985, PNAS, 82, 6677–6681). More recently, it has been demonstrated that the chloride channel can be activated in CF cells and that in CF patients it is the regulation of the chloride channel that is defective (R. A. Frizzell et al, 1986, Science, 233, 558–560, M. J. Welsh and C. M. Liedtke, 1986, Nature, 322, 467–470).

The classical approach to the analysis of genetic disease has relied on a knowledge of the affected protein as in sickle cell anaemia and the thalassaemias. Where the nature of the defective protein is unknown, reverse genetics must be used as exemplified in the analysis of chronic granulomatous disease (B. Royer-Pokora et al, 1986, Nature, 322, 32–38, S. H. Orkin, 1986, Cell, 47, 845–850). In this approach, the chromosomal localisation of the mutant gene is determined by karyotyping or linkage studies. Subsequent cloning and examination of the DNA sequences in the region allows the isolation of candidate genes which can be tested for their involvement in the disease.

Little progress was made in the analysis of CF until 1985 when linkage between CF and the enzyme paraoxonase was reported (Eiberg et al, 1985, Clin. Genet., 28, 275–271). Shortly afterwards, linkage to the probe DOCRI 917 was reported at a distance of 15 centiMorgans (Tsui et al, 1985, Science, 230, 1054–1057) and the probe was shown to map to chromosome 7 by hybridisation to a panel of mouse/human hybrids (Knowlton et al, 1985, Nature, 318, 381–382). Three other RFLP markers for chromosome 7 were found to be linked to CF at a much closer genetic distance of ~1 centiMorgan. Two of these markers were derived from the met oncogene locus (Dean et al, 1985, Nature, 318, 385–388, White et al, 1985, Nature, 318, 382–384). The third marker, J3.11, was an anonymous chromosome 7 marker (Wainwright et al, 1985, Nature, 318, 384–385). The discovery of tightly linked markers opened the possibility of DNA based prenatal diagnosis and carrier testing for the disorder, in families with a history of the disease. For this purpose, it was necessary to determine the recombination frequency between met, J3.11 and CF. This was accomplished in a collaborative study of over 200 families. The study confirmed that both met and J3.11 were within 1 cM of the CF gene and gave strong support for the order met-CF-J3.11 (Beaudet et al, 1986, Amer. J. Hum. Genet. 39, 681–693; Lathrop et al, 1988, Amer. J. Hum. Genet., 42, 38–44). However, there is no direct relationship between genetic distance and physical distance. In fact, there are differences in recombination frequency between male and female and there are areas of the genome where the recombination frequency is very much higher than average (Barker et al, 1987, PNAS, 84, 8006–8010).

Additional markers showing linkage to CF have been isolated such as the COL1A2 collagen gene (Scambler et al, 1985, Lancet ii, 1241–1242) and the anonymous probes 7C22 (Scambler et al, 1986, Nucleic Acids Research, 14, 1951–1956) and B79 (Estivill et al, 1986, Hum. Genet., 74, 320–322). While these probes were sometimes useful in prenatal diagnosis, they were too remote from the CF locus to be useful in localising the gene. Systematic screening of a chromosome 7 library resulted in the isolation of a further 63 RFLP markers in linkage to the CF locus (Barker et al, 1987, PNAS, 84, 8006–8010). Twelve of these markers were within 15 cM of the CF locus, but none of them mapped to the interval between met and J3.11. None of these probes have been made publicly available.

In an attempt to isolate markers closer to the CF gene, Collins et al (1987, Science, 235, 1046–1049) constructed a human chromosome jumping library which enabled them to jump from a Not 1 site in the met G gene to a Not 1 site located 100 kb 3' to the starting point, providing a probe CF63. Similar approaches have been described by Michiels et al, 1987, Science, 236, 1305–1308 and Poustka et al, 1987, Nature, 325, 353–355. In this context the J3.11 locus is regarded as lying in the 3' direction from the Met locus as illustrated in FIG. 6 of this application.

A second strategy has been to search for HTF islands. HTF islands (Hpa II Tiny Fragments) are regions of DNA that contain a large number of unmethylated CG dinucleotide pairs including many cleavage sites for rare cutting restriction enzymes. HTF islands are associated with the 5' end of many but not all mammalian gene sequences (Bird, 1986, Nature, 321, 209–213; Lindsay and Bird, 1987, Nature, 327, 336–338). Williamson et al have used chromosome mediated gene transfer to produce a cell line which only contains a section of human chromosome 7 adjacent to the met oncogene (Scambler et al, 1987, Nucleic Acids Research, 14, 7159–7174). A potential disadvantage to this approach is that the activated met oncogene is known to contain sequences from chromosome 1 (Park et al, 1987, Cold Spring Harbor Symposium Quantitative Biology, 51, 967–975). A cosmid library which is not publicly available was prepared from this cell line and a cosmid containing an HTF island was identified (Estivill et al, 1987, Nature, 326, 840–845). Three markers, XV2C, CS7 and KM19 were subcloned from the cosmids and were found by chance to be in strong linkage disequilibrium with CF. The observed linkage disequilibrium was sufficiently strong to allow partial prediction of carrier status from haplotype analysis. For example, 85% of CF chromosomes in Northern Europe possess the ++ haplotype with the KM19 Pst1 polymorphism (Estivill et al, 1987, Genomics, 1, 257–263). The observed haplotype frequencies are different in Southern European populations suggesting that more than one mutation may be be responsible for CF (Estivill et al, 1988, Am. J. Hum. Genet., 43, 23–28). Diagnoses were originally performed by Southern blot analysis but the amplification of the CS7 and KM19 loci by PCR has been described recently (Williams et al, 1988, Lancet ii, 102–103; Feldman et al, 1988, Lancet ii, 102). Only the sequences of the amplification primers were disclosed in these publications. The complete sequence of CS7 has been disclosed in UK Patent Application GB 2 203 742 A and in Wainwright et al, 1987, EMBO J, 7, 1743–1748. Analysis of recombinant families indicates that the gene lies between KM19 and J3.11 (Farrall et al, 1988, Am. J. Hum. Genet., 43, 471–475). Further screening of the cosmid library has identified an additional marker, D9, which is in linkage disequilibrium with CF and has been claimed to be situated ~160 kb from KM19 towards J3.11 (Estivill et al, 1989, Am. J. Hum. Genet., 44, 704–710). No details of the sequence of D9 have been published and it is furthermore believed that the teaching and experimental detail contained in the above relevant references does not enable the skilled man to derive any further information concerning the D9 locus.

Rommens et al (1988, Am. J. Hum. Genet., 44, 645–663) have isolated a large number of RFLP markers from a chromosome 7 specific library. A total of 258 chromosome 7 specific single copy segments were identified of which 53 were localised to the 7q31–32 region. Two of these markers, D7S122 and D7S340, are in close linkage disequilibrium with CF and map between Met and J3.11. Subsequent analysis showed that D7S340 is located very close to the HTF island detected by CS7. No further details of D7S122 and D7S340 have been disclosed and they are not available to the general public.

Iannuzzi et al have described the use of a 100 kb general jumping library to isolate additional markers (Iannuzzi et al, 1989, Am. J. Hum. Genet, 44, 695–703). A jump of ~100 kb from J3.11 towards met has been described. The clone (W32) detects a Sac II polymorphism but is not in linkage disequilibrium with CF. Again this probe is not publicly available and no further useful characterisation has been published. Additional walks from W32 and D7S340 have since been described (Collins, April 1989, Cold Spring Harbor Meeting on Genome Mapping and Sequencing, Abstract 1349). Four jumps (J16, J17, J44, J18) cover a region of ~280 kb from D7S340 and four jumps (J32,J35, J46,J30) cover a distance of ~400 kb from J3.11. Yet again none of this series of markers have been made publicly available.

Conventional gel electrophoresis cannot resolve DNA fragments greater than 50 kb. Recent developments in Pulsed Field Gel Electrophoresis (Anand, 1986, Trends in Genetics, 2, 278–283; Southern et al, 1987, Nucleic Acids Research, 15, 5925–5943; Carle and Olson, 1984, Nucleic Acids Research, 12, 5647–5664) have permitted the analysis and resolution of DNA fragments of >1 megabase. Combined with the availability of infrequently cutting restriction enzymes such as Not 1 and BssH II, this provides a potential method of relating the genetic map to physical distance. Several groups have prepared maps of the CF locus (Poustka et al, 1988, Genomics, 2, 337–345; Drumm et al, 1988, Genomics, 2, 346–354; Fulton et al, 1989, Nucleic Acids Research, 17, 271–284). There was vague agreement between the three groups but there are inherent difficulties in constructing a map or locating a gene by this method. The methylation state of various cell lines or blood cells will result in different restriction patterns. The mobility of DNA fragments is dependent on sample loading and electrophoresis conditions rendering comparisons between experiments difficult. Thus, the CF gene has been localised to the region between the markers CS.7 and J3.11. Estimates of the distance between the two markers vary from 700–1350 kb (Poustka et al, 1988, Genomics, 2, 337–345) reflecting the inherent inconsistencies of the method.

It will be appreciated that long range mapping by PFGE is unlikely to give results which are reproducible even by the man skilled in the art when starting from published experiments. Thus although chromosome jumps to J16, J17, J44, J18, J32, J35, J46 and J30 have been documented as described above, it is not believed to be possible to localise the resultant markers with any precision. Given the inherent variability of jumping libraries and the inconsistencies of PFGE it would not be posssible for the skilled man to reproduce the experiments of, for example Iannuzzi et al with a view to independently isolating the series of markers described.

A limitation of the PFGE technique has been that the information obtained by PFGE could not be verified since large DNA fragments could not be cloned directly. Although techniques were available for cloning large tracts of DNA as many overlapping segments,the process was time consuming and prone to error. The recent development of Yeast Artificial Chromosomes (YACs) has provided a means of cloning large (100–1000 kb) fragments of DNA in a stable form (Burke et al, 1987, Science, 236, 806–812; Anand et al, 1989, Nucleic Acids Research, 17, 3425–3433; Brownstein et al, Science, 1989, 244, 1348–1351). However, there remain several technical difficulties in the making and screening of YAC libraries which have prevented the general application of the technique (Ianuzzi et al, 1989, Am. J. Hum. Genet., 44, 695–703).

SUMMARY OF THE INVENTION

The present invention provides yeast artificial chromosomes (YAC)s which include nucleotide sequences for use in the detection of cystic fibrosis alleles as well as for use in the diagnosis and therapy of cystic fibrosis. These have been deposited with the National Collection of Industrial and Marine Bacteria (NCIMB), PO BOX 31, 135 Abbey Road, Aberdeen AB9 8DG, Scotland prior to the filing of this patent application. The accession numbers of the yeast artificial chromosomes of the present invention are as follows:

| YAC clone | Accession Number | Size | YAC Ref No. |
|---|---|---|---|
| SC/14DC12 | 40204 | 500 kb | YAC A |
| SC/35FB6 | 40209 | 340 kb | YAC B |
| SC/37AB12 | 40302 | 310 kb | YAC C |

Therefore in a first aspect of the present invention we claim a method for the detection of the presence or absence of one or more inherited disease alleles in sample dna from an individual by determining the presence or absence of a variant nucleotide sequence at a genetic locus 3' of locus a as hereinafter defined and 5' of locus B as hereinafter defined and comprised in one or both of YAC A and YAC B:

Locus A (i)
CGGGTAGCCG GCTGTTATGG TATTCATTTG ATCTAGCCCT AATGTAATCT TGTCAACCAG 60

GTGGTCTTTT CCTTTTGCTT CAAATAGACT TTAGGTGCTC TTAAAATTTT CAGCATCCTA 120

TAGTACTAAC CTAAATTTTC AGCATCCTAT 150

(ii)
GACTCAATGT GAAGTGACTA AATTCTGGTG AGTATGGCTG AGAGGTTGAG GATCTCTCCT 60

TTCACTGAGC ACCATAGGAT GAGANNNNTT CTCCCAGACA 100

Sequences (i) and (ii) are respectively the 5' and 3' termini of a novel 800 bp marker sequence 3' to the KM19 PCR product (Lancet ii, 102, 1988). N represents a nucleotide of unknown identity.

Locus B (i)
GTGCTATGAG TCACCTCCAG CCCACCACTG TTTGAATGGT ATTTAAAGTG AAGGTACAGA 60

AGCTATTTWA AAGGTCACAG AAGTAACCTA GGCAAGTGAT AAAGAGACTA AATTAAGGTA 120

GCAGAAATAG GAGAGACTAT TT 142

(ii)
ATGCCTGCAG GTCGACTCTA GAGGATYCCC CTAGAGCATA TAAAATTATT TTCAAGGGAA 60

GATGTAAAAA TAGGTATGAA GAAGTTCTGG TACTTTTTTC CCCACCCAGC AGATCACTGT 120

TTTTTTTTTT TTNTTTTTTT TTTTTTTTTT TATCACTTGA GTGTTATGCA CTGCTCTTTA 180

Sequences (i) and (ii) are respectively the 5' and 3' termini of a novel 950 bp marker sequence 5' to the probe J3.11 (Bartels et al, Am. J. Hum. Genet., 38, 280–287, 1986). W represents A or T/U and Y represents C or T/U.

The genetic locus of interest is conveniently comprised in YAC A.

In a further aspect of the present invention we claim a method for the detection of the presence or absence of one or more inherited disease alleles in sample DNA from an individual by determining the presence or absence of a variant nucleotide sequence comprised in YAC C.

In respect of the above aspects of the invention the inherited disease is preferably cystic fibrosis.

In a convenient aspect of the present invention we provide a method for the detection of one or more inherited disease alleles in sample nucleic acid from an individual which method comprises determining whether or not an allele of a genetic locus comprised in one or both of YAC A and YAC B and 3' of locus A and 5' of locus B in sample nucleic acid from a member of the individual's family, has been inherited in a manner consistent with the presence of an inherited disease allele in sample nucleic acid from the individual to be tested. YAC A, YAC B, locus A and locus B are as hereinbefore defined.

The genetic locus of interest is conveniently comprised in YAC A.

In a further convenient aspect of the present invention we provide a method for the detection of one or more inherited disease alleles in sample nucleic acid from an individual which method comprises determining whether or not an allele of a genetic locus comprised in YAC C as herein defined in sample nucleic acid from a member of the individual's family has been inherited in a mannet consistent with the presence of an inherited disease allele in sample nucleic acid from the individual to be tested.

In respect of the above convenient aspects of the present invention the inherited disease is preferably cystic fibrosis.

An allele is defined as a variant of a genetic locus and is inherited according to conventional principles of genetic segregation. An allele of a genetic locus may be characterised according to its size or composition or both size and composition. It will be appreciated that the allelic variation at a genetic locus may be as little as a single base pair alteration and such variation can be readily detected according to the present invention as hereinafter described and such variation can determined for example using known methods.

Informative variation within a genetic locus may arise from variation within an inherited disease associated gene itself or within a nucleotide sequence at a distance from but genetically linked to the inherited disease associated gene. In general, diagnosis of variations within the inherited disease associated gene itself are preferred as this eliminates the possibility that genetic recombination events have occurred which compromise the usefulness of the linked genetic marker. Informative variation at a linked genetic marker may conveniently arise from the presence of a variable number of tandem repeats of a nucleotide sequence. Examples of such regions include minisatellite regions wherein a nucleotide sequence of for example up to 50, 40, 30, 20, or up to 10 bases is repeated, for example as described in Am. J. Hum. Genet., 43, pages 854–859 (1988) by Nakamura et al, or a microsatellite region wherein a nucleotide sequence of up to 5, 4, 3 or up to 2 bases is repeated, for example dinucleotide repeats such as (CA)n repeats or regions complementary thereto as described in Am. J. Hum. Genet., 44, pages 397–401, (1989), Litt et al and Am. J. Hum. Genet., 44, pages 388–396, (1989), Weber et al. Alternatively informative variation may arise from changes which affect sample nucleic acid cleavage, for example changes in the nucleotide sequences recognised by restriction enzymes. Such changes are conveniently detected as restriction fragment length polymorphisms (RFLPs) or may be identified using any other method for the detection of sequence variation. The method of the present invention may also be performed using any product derived from the genomic DNA sequences such as RNA, for example MRNA, as well as peptides such as polypeptides and proteins. It will be appreciated that such derived products may be detected using methods known in the art.

The determination of whether or not an allele of a genetic locus 3' of locus A as hereinbefore defined and 5' of locus B as hereinbefore defined and comprised in one or both of YAC A and YAC B, conveniently YAC A, or more conveniently in YAC C, in sample nucleic acid from a member of the individual's family, has been inherited in a manner consistent with the presence of an inherited disease allele in sample nucleic acid from the individual to be tested is conveniently effected by contacting sample nucleic acid with polynucleotide(s) capable of distinguishing alleles of said genetic locus.

The above determination is conveniently employed for the detection of cystic fibrosis alleles.

The polynucleotide(s) may be capable of distinguishing alleles of the genetic locus for example either as polynucleotide probes or as primers for possible extension. The polynucleotide(s) can be DNA, RNA or any other kind hybridisable to DNA. The polynucleotide(s) are conveniently DNA. The nucleic acid can be in double stranded or single stranded form, conveniently single stranded and may include modified bases such as hypoxanthine or deazaguanine such as 7-deazaguanine.

The polynucleotide probes can be prepared by microbiological reproduction of cloned material or by direct synthesis. The probe may include label or marker components and is then conveniently $^{32}P$ radiolabelled in any conventional way, but can alternatively be radiolabelled by other means well known in the hybridisation art for example to give $^{35}S$-radiolabelled probes. The nucleotide may also be labelled with non-radioactive species such as biotin or a similar species by the method of D C Ward et al, as described in Proceedings of the 1981 ICN-UCLA Symposium on Developmental Biology using Purified Genes held in Keystone, Colo. on Mar. 15–20, 1981 vol. XXIII, pages 647–658, Academic Press; Editor Donald D Brown et al, or even enzyme labelled by the method of A. D. B. Malcolm et al, Abstracts of the 604th Biochemical Society Meeting, Cambridge, England (meeting of Jul. 1, 1983. Further and particularly convenient methods of non-isotopic labelling are described in our European patent application, publication no. 207758.

The polynucleotide probes will hybridise selectively under appropriate conditions to different alleles of a genetic locus. Suitable hybridisation conditions will depend on the relevant nucleotide sequences but can be readily determined by the skilled man, for example after appropriate routine experimentation. Thus, for example, the polynucleotide sequences may be complementary to either variant nucleotide sequences indicative of one or more inherited disease alleles or to nucleotide sequences indicative of normal alleles. Dot Blot hybridisation provides a convenient method for the detection or absence of a hybridisation product.

Polynucleotide probes as outlined above comprise a further aspect of the present invention. Their nucleotide sequence is of any convenient length such as up to 50, 40, 30 or 20 nucleotides, for example comprising at least 6, 8, 10, 12, 14, 15, 16 or 18 nucleotides. Conveniently their nucleotide sequence comprises 10–25, 15–20, 17–19 or 18 nucleotides. It will be appreciated that longer nucleotide sequences may require the inclusion of destabilising nucleotides. Appropriate sequences may be determined by routine experimentation.

Sample genomic DNA may be fragmented for example using enzymes such as restriction enzymes prior to hybridisation with probe(s). The nucleic acids may then be separated according to molecular weight and conveniently using gel electrophoresis for example on a solid support. Hybridisation with probe(s) is then carried out, for example using Southern Blot hybridisation. Where the probe used is radiolabelled, autoradiography is a convenient method of detection. Where a sufficient amount of probe-nucleic acid hybrid is available, direct methods for visualisation of hybrids may be used. These include the use of dyes, for example intercalating dyes such as ethidium bromide to enable visualisation of the hybrids.

If required the sample genomic DNA may be amplified. Extension of a nucleic acid primer on a DNA template provides an extension product comprising a nucleotide sequence complementary to the nucleotide sequence of the relevant DNA. Convenient amplification methods include polymerase mediated chain reactions such as those disclosed by K. Kleppe et al in J. Mol. Biol., 1971, 56, 341–361 and those disclosed in U.S. Pat. Nos. 4,683,195 and 4,683,202 or alternatively Q-beta replicase as described in PCT Patent application, publication WO-87/06270 and in Biotechnology, Vol 6, October 1988 may be used. Additionally transcription based nucleic acid amplification described in PCT Patent application, publication WO-88/10315 (Siska Corporation) may be used. Alternatively linear amplification, as opposed to exponential amplification for example as obtained via the polymerase chain reaction, may be used. In linear amplification a polynucleotide primer anneals to a sample DNA template, under appropriate conditions the primer is extended as far as required and the extension product is then separated from the template. The above process of primer annealing, extension and separation is repeated as many times as required. It will be appreciated that since primer extension always occurs on a sample DNA template the possibility of inaccurate copies being formed is reduced. The number of cycles required in respect of linear amplification will generally be higher than that for exponential amplification. Generally a primer will comprise at least seven nucleotides, such as 15–40 nucleotides, for example 20–30 nucleotides. The maximum length of any primer is not believed to be critical and is only limited by practical considerations.

As mentioned previously polynucleotide(s) may be capable of distinguishing alleles of the genetic locus when acting as primers for possible extension. Appropriate primers are prepared as for sample DNA amplification as described above. Alleles of a genetic locus are preferably detected using the technique referred to as the amplification refractory mutation system (ARMS) as described in Nucleic Acids Research, 17, 7, 1989, pages 2503–2516 and claimed in our European Patent Application, Publication No. 332435. ARMS employs a diagnostic primer substantially complementary to a diagnostic region so that under appropriate conditions the identity of a terminal nucleotide being either a normal or variant nucleotide may be detected by reference to the formation or non-formation of an extension product. Both polymerase chain reaction (PCR) and linear amplification may be used with this technique. The expression "diagnostic portion" means that portion of a target base sequence which contains a nucleotide as its terminal nucleotide the potential variant nucleotide, the presence or absence of which is to be detected. Generally the potential variant nucleotide will be at the 3'-terminal end of the diagnostic portion since in general synthesis of primer extension products will be initiated at the 3' end of each primer as described above. Where however an agent for polymerisation is to be used which initiates synthesis at the 5' end of the diagnostic primer and proceeds in the 3' direction along the template strand until synthesis terminates the "diagnostic portion" will contain the potential variant nucleotide at its 5' end. The diagnostic primers will also be appropriately designed in this regard as set out below. The target base sequence means a nucleotide sequence comprising at least one diagnostic portion. Thus for example in a single test all the known diagnostic regions may be tested for the presence or absence of variant nucleotides. The primers are selected to be "substantially" complementary to the different strands of each specific sequence to be amplified. This means that the primers must be sufficiently complementary to hybridize with their respective strands. Therefore, the primer sequence need not reflect the exact sequence of the template. For example, where the diagnostic primer comprises a nucleotide sequence in which the 3'-terminal nucleotide is complementary to either the suspected variant nucleotide or the corresponding normal nucleotide a non-complementary nucleotide fragment may be attached to the 5'-end of the primer, with the remainder of the primer sequence being complementary to the diagnostic portion of the target base sequence. Commonly, however, the primers have exact complementarity except in so far as non-complementary nucleotides may be present at a predetermined primer terminus. It will be appreciated, however, that in certain circumstances (for example at reduced temperature or perhaps where the diagnostic primer is particularly rich in G (guanine) and C (cytosine) residues) then hybridisation of the diagnostic primer and synthesis of its extension product might be induced to occur even in the presence of a non-complementary 3'-terminal residue. This artefactual result is avoided by increasing the temperature of reaction, decreasing the salt concentration or deliberately introducing one or more further mismatched residues within the diagnostic primer to further reduce hybridisation.

Extended primers may be detected not only by the use of appropriate probes but also by direct methods not requiring the use of probes, for example products of a given size may be directly visualised or products may firstly be separated according to molecular weight for example using gel electrophoresis prior to detection, for example by visualisation.

Diagnostic primers may be used in any appropriate aspect of the present invention. Additionally an amplification primer corresponding to each diagnostic primer is preferably provided the nucleotide sequence of the amplification primer being such that any extension product of the corresponding diagnostic primer may, after separation from its complement, serve as a template for synthesis of an extension product of the amplification primer.

The polynucleotide probes or diagnostic primers of the present invention may be provided in a kit together with appropriate instructions and/or inserts and conveniently together with test or control DNA. These comprise further aspects of the present invention. In respect of diagnostic primers the kit will conveniently comprise a diagnostic primer for each diagnostic portion of a target genomic DNA sequence together with each of four different nucleoside triphosphates; and an agent for polymerisation of the nucleoside triphosphates. Preferably the kit of the present invention additionally comprises an amplification primer corresponding to each diagnostic primer the nucleotide sequence of the amplification primer being such that any extension product of the corresponding diagnostic primer may, after separation from its complement, serve as a template for synthesis of an extension product of the amplification primer. Each of the materials detailed above and/or the amplification primer may be conveniently packaged in a separate container, but preferably all may be combined in a single container to which the material to be analysed is added. Advantageously the single container will additionally contain buffer.

Alleles of a genetic locus may for example be detected by direct nucleotide sequencing of a genetic locus 3' of locus A as hereinbefore defined and 5' of locus B as hereinbefore defined and comprised in one or both of YAC A and YAC B, conveniently in YAC A and more conveniently in YAC C. As mentioned earlier above, methods and materials for carrying out nucleotide sequencing will be immediately apparent to the molecular biologist of ordinary skill, for example using methods analogous to those outlined in Nucleic Acids Research, 16, 8233–8243, 1988, Newton et al; and Nature, 1988, 332, 543–546, Higuchi et al.

An important and preferred approach to examination of the yeast artificial chromosomes of the present invention is the use of the invention described in our European patent application no. 89307672.9, publication no. 356021 to characterise the nucleotide sequence of any one of the YACs of the present invention. The above European patent application was unpublished at the priority date of this application. The invention described therein relates to a method for the amplification of nucleotide sequences and kits therefor. Such a method is of particular interest in relation to the amplification of sequences only a portion of which is known and enables long nucleotide sequences to be rapidly and efficiently sequenced. The method avoids the recombinant DNA cloning procedures hitherto necessary for the sequencing of unknown nucleotide sequences. By so doing it also allows polymorphisms between nucleotide sequences of different alleles at a genetic locus to be detected as well as the simultaneous analysis of alleles at a particular locus in different individuals. The prior art technique of "chromosome walking" involves a number of potential difficulties as is exemplified by the time taken from discovery of a marker for a genetic disorder to discovery of the specific genetic lesion responsible for the disorder. Thus, for example, a linked genetic marker for Huntington's Chorea (D4S10) was discovered in 1983, but still today the specific genetic lesion responsible for this disorder is not known. Similar comments apply to many other genetic disorders. The technique of "chromosome walking" particularly suffers from the disadvantage that cloning of genomic DNA is a prerequisite. In a number of circumstances cloning may prove impossible or at least very difficult and in such situations the "chromosome walk" comes to a premature end; A. R. Wyman and K. F. Wertman, in Methods in Enzymology, Vol 152, S. L. Berger and A. R. Kummel, editors, Academic Press, San Diego, 1987, 173–180. Moreover the analysis of the fragments identified as representing overlapping clones is complex in view of inter alia the number of such fragments which may be located in any one screening of the genomic library and the fact that the overlapping sequences may be in either the 5' or the 3' sense.

The invention, for example as now disclosed and claimed in EP-A-356021, provides a method for the amplification of a nucleic acid fragment, comprising unknown sequence, by primer extension which method comprises cleaving a target nucleic acid to obtain target nucleic acid fragments, one of said fragments containing an initiating priming region of known nucleotide sequence for hybridisation with an initiating primer, preparing target nucleic acid fragment/ vectorette units from the target nucleic acid fragments by ligation each unit having a vectorette priming region of known sequence for hybridisation with a vectorette primer, and treating the target nucleic acid fragment/vectorette units, together or sequentially, with appropriate nucleoside triphosphates and an agent for polymerisation of the nucleoside triphosphates under hybridising conditions, such that an extension product of an initiating primer is synthesised complementary to a single stranded target nucleic acid/ vectorette unit having an initiating priming region to which is hybridised an initiating primer selected so as to be substantially complementary to the initiating priming region, whereas no such extension product is synthesised complementary to single stranded target nucleic acid fragment/vectorette units having no such initiating priming region.

If desired the said extension product may be subjected to amplification in the presence of a vectorette primer which is selected so as to be substantially complementary to the vectorette priming region. The target nucleic acid fragment/ vectorette units are thus treated with initiating primer and, if the initiating primer extension product is to be amplified for example as described by R. K. Saiki et al, Science, 239, 487–491 (1987), additionally treated with vectorette primer. Where no vectorette primer is used, arithmetical or linear amplification (hereinafter referred to as linear amplification) may be achieved by hybridisation of the initiating primer to the initiating priming region followed by primer extension in the presence of appropriate nucleoside triphosphates and an agent for polymerisation of the nucleoside triphosphates, under hybridising conditions and denaturation. This process of priming, primer extension and denaturation may be repeated as many times as appropriate to achieve the desired level of amplification. Preferably, however, amplification is effected in the presence of both initiating and vectorette primer by the use of the polymerase chain reaction (PCR) technique.

A vectorette priming region may be present or absent from the vectorette portion of a target nucleic acid fragment/ vectorette unit. Thus a vectorette may itself contain no vectorette priming region provided that in use a target nucleic acid fragment/vectorette unit is formed in which the vectorette portion thereof contains a vectorette priming region. Thus such units may for example either have a vectorette priming region in the vectorette portion of the target nucleic acid fragment/vectorette unit as formed by ligation or have a vectorette priming region which only arises as a result of primer extension of an initiating primer as described hereinafter. The target nucleic acid fragment/ vectorette units may be prepared for example either directly from the desired species or indirectly from such a species after initial cloning in plasmid, phage, cosmid or yeast artificial chromosome (YAC) vectors. The nucleotide sequences are preferably from genomic DNA, but may be from sorted chromosomes or more preferably from yeast artificial chromosomes as hereinbefore described.

Different vectorette libraries may be prepared from the same target nucleic acid by cleavage with different restriction endonucleases and ligation of suitably adapted vectorette portions to generate target nucleic acid fragment/ vectorette units. All available restriction endonucleases can be used in this process if desired and in the limit a vectorette portion can be ligated to target nucleic acid fragments at every restriction enzyme recognition site in the target nucleic acid. This feature is not always desirable as ideally the initiating priming region of interest in any given vectorette library will be separated by 100 bp or more from the attachment point of the vectorette portion. This is because initiating primer extension products or initiating primer/ vectorette primer amplification products smaller than this generate so little sequence information in the practice of the invention as to be of little value for the efficient sequencing of long nucleotide sequences. Furthermore the nucleotide sequence of such small products will be contained within the products obtained using a vectorette library in which the initiating primer is further from the vectorette portion attachment site. The use of a plurality of different vectorette libraries with a particular initiating primer allows identification of those libraries wherein the extension or amplification products are of a convenient size for sequencing. For example it may be particularly convenient to select initiating primer extension or amplification products of approximately 200 bp, 400 bp, 600 bp, 800 bp, 1000 bp and so on obtained from particular vectorette libraries with a given initiating primer. Sequencing of such products, from the vectorette libraries in which they happen to occur for a given initiating primer, using a vectorette or nested vectorette sequencing primer and methods known per se is likely to generate overlapping sequence data for a large region to the 3'-side of the initiating primer. The amount of sequence data generated in one round of analysis of a plurality of vectorette libraries with a given initiating primer is only limited by the size of initiating primer extension or amplification products which can be obtained in practice and/or by the distance (from the imitating primer region) to the most remote restriction endonuclease site represented in the plurality of vectorette libraries.

If desired one or more of said initiating primer extension products may be isolated and/or sequenced or at least a portion of the extension product may be sequenced. Thus for example this embodiment may be conveniently used to identify a desired, normally the longest, target nucleic acid fragment containing an initiating priming region, so that the 3' terminal end may be sequenced conveniently with a nested vectorette primer as hereinbefore described in order to provide a new start point for further use of the method of the present invention such as this preferred embodiment. The sequence of the 3' terminal end of the aforementioned longest target nucleic acid fragment may thus become the initiating priming region of a new target nucleic acid fragment for a further round of vectorette library multiple initiating primer extension product formation, identification of the longest target nucleic acid fragment and sequencing.

In selecting a new initiating priming region on the basis of novel sequence data generated using the method of the invention at the 3' terminal end of a target nucleic acid fragment such sequence data may routinely be compared with the publicly available database compilations of known nucleic acid sequence (for example Genbank, EMBL) so as to ensure that a proposed new initiating priming region does not by chance closely match a known nucleic acid sequence elsewhere in for example the genomic DNA of interest. This is obviously most likely to occur in those cases where the 3'-termiqal end of a particular target nucleic acid fragment happens to comprise repetitive elements such as for example Alu sequences. In such cases it is advantageous to perform the method of the invention on a plurality of vectorette libraries with a given initiating primer so as to guarantee that at least one of the resulting extension products has a non-repetitive/unique 3'-terminal end for the selection of a further initiating priming region.

Stepwise progression from one previously unknown initiating priming region to another along a target nucleic acid, for example human genomic DNA, may conveniently be monitored using samples of the said target nucleic acid separately cleaved to completion with the same restriction endonucleases as used in the preparation of target nucleic acid fragment/vectorette units ("vectorette libraries" as hereinbefore defined) and subjected to agarose gel electrophoresis and Southern Blotting. Probing of the filters so obtained with a first initiating primer will reveal a pattern of bands consistent with the various restriction enzyme recognition sites surrounding this first initiating priming region in the target nucleic acid. Use of the method of the present invention with a plurality of vectorette libraries and this first initiating primer will generate a series of extension products each of whose 3' terminal ends are defined by the position relative to the initiating priming region of the closest recognition site for the restriction enzyme used to generate the vectorette library in question. Thus a map of the restriction sites to the 3' side of a first initiating primer is effectively obtained. Having subsequently selected a second novel initiating priming region of previously unknown sequence, linkage to the first initiating priming region is established by reprobing the above Southern Blot filter with the second novel initiating primer. The pattern of bands obtained will be identical to that obtained with the first initiating primer in those cases where no recognition site for the restriction enzyme in question lies between the first and second initiating priming regions. In those cases where a recognition site for the restriction enzyme in question does occur between the initiating priming regions as judged by the appearance of smaller extension products in the corresponding vectorette library, then a fragment of different size will normally be observed on reprobing the Southern Blot filter with the second initiating primer. By repetition of this method consistency, accuracy and reliability of stepwise progression from one initiating priming region to another along a target nucleic acid is maintained and assured.

It will be appreciated that the sequence of the 3'-terminal ends of all the plurality of initiating primer extension products may be easily obtained using the same vectorette primer or nested vectorette primers for sequencing by methods known per se. In this way the entire sequence of an unknown segment of target DNA nucleic acid may be determined in a facile and systematic manner and with much greater convenience than for example using M13 "Shotgun" cloning. This is because the initiating primer extension products can be ordered by size and therefore the order of their sequences in the original target nucleic acid becomes apparent.

Each initiating primer extension product shares a 5'-extremity determined by the initiating primer and a 3'-extremity determined by the closest 3'-site for the particular cleavage means, for example restriction enzyme, used in the synthesis of that particular vectorette library.

In a preferred embodiment of the present invention any or all of the initiating primer extension products obtained is (are) sequenced (as hereinafter defined) at least at the end(s) distal to a given initiating primer so as to determine the sequence of a further initiating primer whereby to obtain further initiating primer extension products based on primer extension of the further initiating primer.

In a further preferred embodiment according to the present invention an initiating primer extension product or portion thereof is sequenced (as hereinafter defined) whereby to characterise the said extension product or portion thereof.

As described above one important application of the present invention is the identification of a previously unidentified genotype, for example a genetic defect(s) responsible for a phenotype, for example a genetic disease or disorder or the identification of a previously unidentified genotype, for example a genetic defect(s) which is (are) responsible for or a contributory factor in predisposition to a phenotype, for example a disease.

Thus for example in relation to a genotype such as a genetic disease or disorder the method of the present invention may be applied to nucleic acid which does not contain the genotype (e.g. genetic defect(s)) and to nucleic acid which does contain the genotype e.g. genetic defect(s) to be investigated, identification of the genotype e.g. genetic defect(s) being effected by comparison of the information generated by sequencing of the two nucleic acid samples. Such comparison might simply be effected, for example, by comparison of the sequencing gels conveniently by automatic scanning. In this regard it will be appreciated that the specific sequences need not be determined per se provided that sufficient data is generated to enable a difference or differences between the target nucleic acid samples to be detected and identified, and the terms "sequencing" and "sequenced" are accordingly used herein to include not only specific nucleotide sequence determination, but also the detection and identification of sequence differences without specific nucleotide sequence determination. It is convenient to apply the method of the invention to the target nucleic acid of an obligate heterozygote for example for the genetic disease or disorder to be investigated. Of necessity both a normal and a mutant allele for the locus in question will be present in such an individual and those sites identified using the method of the invention where more than a single nucleotide is present on sequencing are candidates to be the phenotype, e.g. disease or disorder causing mutation.

In addition to the above it is suspected that certain genotypes e.g. genetic defects may predispose individuals to phenotypes for example diseases such as premature atherosclerosis, hypertension, diabetes and cancer. For example, if such genetic defects could be identified then such "high risk" patients could be monitored and any onset of the disease treated at an early stage. The method of the present invention may be applied to the identification of such predisposing genotypes. Thus for example the method of the present invention may be applied to the nucleic acid of a plurality of individuals affected by a phenotype to be investigated on the one hand for example a subgroup of cystic fibrosis patients who present with meconium ileus, and to the nucleic acid of a plurality of individuals presenting no evidence of the said phenotype on the other hand for example a subgroup of cystic fibrosis patients who do not develop meconium ileus or normal individuals without cystic fibrosis, identification of a genotype being effected by comparison of the sequences of the nucleic acid samples. Conveniently nucleic acid from the plurality of individuals affected by the phenotype to be investigated will be pooled and subjected to the method of the present invention and similarly nucleic acid from the individuals presenting no such evidence of the said phenotype will be pooled and subjected to the method of the present invention. Comparison of the sequence differences between the two pools will identify the presence of any predisposing genotype if any is(are) present. The advantage of this technique is that it enables individual predisposing genotypes to be identified irrespective of their frequency of occurrence and irrespective of the overall complexity and number of different contributory genetic factors to the overall phenotype. Thus if the presence of a combination of apparently unrelated genetic defects are responsible for or represent a contributory factor in the predisposition to a disease to be investigated, the method of the present invention will be able to identify this.

The target nucleic acid fragments may for example be obtained from single individuals known to be normal homozygotes for a given genetic locus for example cystic fibrosis or other inherited disease. The target nucleic acid fragments may also be obtained from groups of individuals (as opposed to single individuals) with a shared phenotype (s) for example cystic fibrosis or some clinical subgroup thereof. The nucleic acid or tissue from each member of a group which shares a phenotype may if desired be pooled. Each group of individuals will consist of at least 2 and advantageously less than 1000, for example 50–500. Vectorette units may be prepared from the pooled target nucleic acid fragments and the vectorette units pooled or used separately to form vectorette libraries. The shared phenotype may if desired be a disease or disease predisposition for example cystic fibrosis, obligate carriage of an inherited disease for example cystic fibrosis or a normal state with no evidence of the disease or disease predisposition.

In summary the vectorette units obtained and amplified according to the above method may be sequenced using either the initiating primer or vectorette primer as sequencing primers. Such novel sequences may be used to isolate further yeast artificial chromosomes which contain sequences which are within and adjacent to those comprised in the yeast artificial chromosomes hereinbefore described and which are 3' to locus A and 5' to locus B. This method was used to identify YAC C starting from YAC A.

Comparison of nucleotide sequences obtained using the above methods will identify any common genetic variants in the population which are associated with, for example cystic fibrosis. Thus, the above mentioned methods which were unpublished at the priority date of this application, when applied to the yeast artificial chromosomes of the present invention allow the skilled man to directly and unambiguously ascertain the nucleotide sequence of all or at least part of the cystic fibrosis gene and its flanking regions. This is conveniently illustrated but not limited by Example 4 of this application. Given that the YACs of the present invention were prepared from an individual thought to be homozygous normal at the cystic fibrosis locus, the sequence derived from these YACs is expected to represent the normal human cystic fibrosis gene.

Therefore in a further aspect of the present invention we claim nucleotide sequences and in particular genetic coding sequences identifiable using the technique of our European patent application number 89307672.9, publication number 356021 as hereinbefore described, and occurring within the yeast artificial chromosomes of the invention. The genetic coding sequence is preferably all or part of the cystic fibrosis gene.

Comparison of the nucleotide sequences of CF genes from affected and unaffected individuals allows the characterisation of all of the different mutations responsible for cystic fibrosis.

In addition it has unexpectedly been found that the nucleotide sequences comprised in the yeast artificial chromosomes of the present invention may be used as hybridisation probes for example for the detection of inherited disease alleles and preferably cystic fibrosis alleles. This is conveniently illustrated but not limited by Example 4 of this application. It has unexpectedly been found that probes may be conveniently provided by the removal of repetitive sequences from the chosen YAC nucleotide sequence. Removal of repetitive sequences is conveniently accomplished by reassociation for example in the presence of excess human DNA.

Therefore according to a further aspect of the present invention there are provided nucleotide sequences of at least 3 kilobases, 5 kilobase, 7 kilobases, 10 kilobases, 50 kilobases, 100 kilobases, 200 kilobases, 300 kilobases, 400 kilobases or up to about 500 kilobases comprised in any one of the YACs of the present invention and 3' to locus A as hereinbefore defined and 5' to locus B as hereinbefore defined. The nucleotide sequence may have an optional label or marker component when used as a hybridisation probe.

In a further convenient aspect of the invention we provide a hybridisation probe which comprises a terminal nucleotide sequence of a YAC of the present invention. The hybridisation probe more conveniently comprises the left hand terminal sequence of YAC A:

```
AAGCAAGTTA TTGTGTTATG CACTCTATAA GGGACAGAAA ACTTAGTAAG AAAAAATCTG   60

TTTTATCTAG CATTTCTATT ACATTCTTTA TCTAGCCTGC TTTAATTGGT GATGATTTTG  120

TGTTTAAACC TTGCTTTCTT AACTAGGATA CCTGCAAGTA TTTACAATGC TAAGTGGAAA  180

TTA AA                                                                          185
``` or any polynucleotide which specifically identifies the genetic locus comprised by the above sequence.

The above polynucleotides or polynucleotide probes may be used to probe genomic DNA which has conveniently been cleaved to provide DNA fragments of a convenient size. This is conveniently acheived by the use of one or more restriction endonucleases. In respect of YAC A convenient restriction endonucleases include Sst II and Not I. Restriction fragments which hybridise to the probes of the invention can then be excised from for example a PFGE gel and used for subcloning and sequencing. Thus the above polynucleotides or polynucleotide probes which specifically identify the left hand terminal sequence of YAC A may be conveniently used to hybridise to single Sst II or Not I fragments which can then be isolated as described above and used for subcloning and sequencing.

The yeast artificial clones of the present invention may also be used to prepare a cosmid, phage or plasmid DNA library. For example a gel purified YAC of the invention, conveniently from a low melting point agarose gel, is restricted with, for example, 6 bp recognition sequence restriction enzymes to generate small DNA fragments which can then be subcloned into plasmid or bacteriophage vectors to generate clones corresponding to DNA from within the YAC of interest. These clones can then be sequenced using methods known per se to provide additional information within the YAC. The YAC is conveniently YAC A.

In a further approach the above cosmid, phage or plasmid library may be screened with a probe to identify a variable number of tandem repeats of a nucleotide sequence for example as hereinbefore described and in particular a dinucleotide probe such as an (AC)n oligonucleotide of for example 10 base pairs to 5 kilobases, such as up to 1, up to 2, up to 3, up to 4 or up to 5 kilobases. This will reveal polymorphisms which may be used in the methods of the present invention. Convenient oligonucleotide probes may be prepared by methods well known in the art. The invention therefore also relates to polynucleotides and polynucleotide probes capable of detecting polymorphisms as outlined above.

In a still further approach the YACs of the present invention may be used to provide transgenic animals and transgenic cell lines. Thus homologous recombination in yeast is used for the incorporation of a selectable marker such as 'neo' into a YAC of the invention, conveniently YAC C. This is for example either directed to the 'alu' repeated sequence elements in the human DNA part of the YAC or to the vector arm (Pavan et al., 1990, Mol. Cell. Biol., 10, 4163–4169). Alternatively, targeting, such as 'neo' targeting is to a specific region of the cloned DNA (Pachnis et al., Proc. Natl. Acad. Sci. 87, 5109–5113). Homologous recombination can also be used to manipulate and alter sequences in the human DNA part of the YAC. Following manipulation and insertion of the selectable marker, the YAC is transferred into mammalian cell lines or ES cells for example by polyethylene glycol mediated spheroplast fusion (Pavan et al., 1990, Mol. Cell. Biol., 10, 4163–4169; Pachnis et al., 1990, Proc. Natl. Acad. Sci., 87, 5109–5113), calcium phosphate co-precipitation (D'Urso et al., Genomics, 7, 531–534; Wigler et al., 1979, Proc. Natl. Acad. Sci., 76, 1373–1376) or microinjection of the purified YAC DNA directly into ES cells. Homologous recombination in the ES cells is identified for example by screening conveniently using the polymerase chain reaction (PCR). The desired cells are then directly injected into a suitable animal such as a mouse or a rat or similar blastocyst for the generation of transgenic animals. Purified YACs with selectable markers can also be injected directly into the fertilised eggs of suitable animals such as mice or rats or similar animals for the generation of transgenic animals. The YACs can also be used for the generation of transgenic cell lines using the methods described above.

Therefore according to a further aspect of the present invention we provide the use of a YAC of the present invention, conveniently YAC C, for the preparation of a transgenic animal and/or a transgenic cell line.

BRIEF DESCRIPTION OF THE DRAWINGS

The invention will now be illustrated but not limited with reference to the following examples and figures wherein.

DESCRIPTION OF THE PREFERRED EMBODIMENTS

EXAMPLE 1

Figure 1:
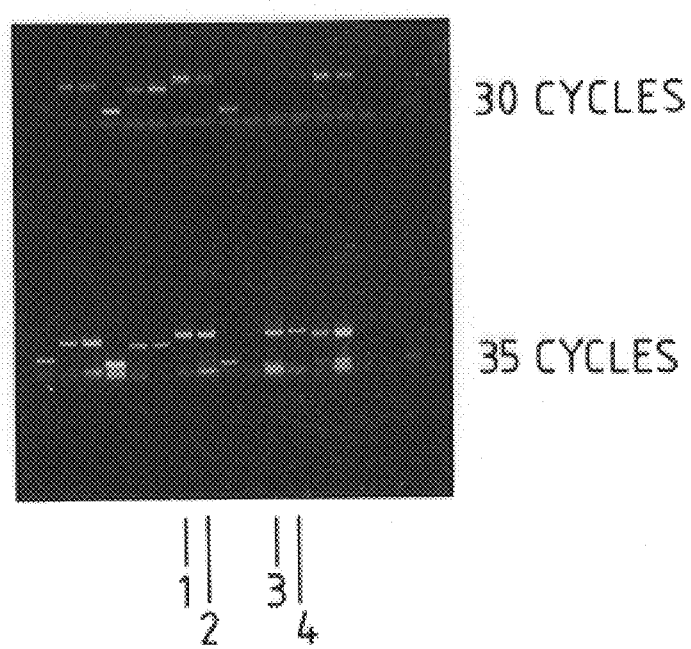
FIG. 1 shows the results of amplification of a YAC vectorette library. Lanes 1 and 2 show a 500 bp product from a HinFI library between primers 1089 and 224. Lanes 3 and 4 show a 500 bp product from a Bgl II library.

Construction of a Yeast Artificial Chromosome (YAC) library:

High molecular weight DNA in agarose plugs was prepared from the human lymphoblastoid cell line GM1416 (48,XXXX) (National Institute of General Medical Sciences Human Genetic Mutant Cell Repository, Camden, N.J.) at a concentration of $1.5 \times 10^7$ cells/ml according to the methods of Schwartz and Cantor (1984, Cell, 37, 67–75). Individual plugs contained ~$1.5 \times 10^6$ cells and therefore had a DNA content of approximately 10 μg. For preparative fractionation, 10 plugs (~100 μg) were equilibrated in a 20 fold excess of 1×TE (10 mM Tris-HCl pH 7.5,2 mM EDTA) for 16 hours at 4° C., followed by two 30 minute washes in 1×TE and a 60 minute wash in a 20× excess of EcoRI restriction buffer at 4° C. The EcoRI buffer is 100 mM Tris-HCl pH 7.5, 50 mM NaCl, 5 mM $MgCl_2$, 100 μg/ml bovine serum albumin or conveniently 50 mM Tris-HCl pH 7.5, 100 mM NaCl, 6 mM $MgCl_2$, 100 μg/ml gelatin. The buffer was replaced by fresh cold buffer plus EcoRI to give a final plug plus buffer volume of 3 ml and an EcoRI concentration of 5 units/ml. The plugs were kept on ice for 30 minutes with occasional mixing to allow the enzyme to equilibrate. They were then incubated at room temperature and one plug was removed every 5 minutes for 30 minutes. Incubation was continued at 37° C. and again one plug was removed every 5 minutes. Digestion was halted by dropping plugs into 40 ml cold TAE (40 mM Tris acetate pH 8.3, 2 mM EDTA) containing 10 mM EDTA.

Pulsed Field Gel Electrophoresis fractionation was performed on a "Waltzer" apparatus as described previously (Southern et al, 1987, Nucleic Acids Research, 15, 5925–5943). DNA fragments >200 kb were selected and gel slices containing DNA were processed as described by Anand et al, 1989, Nucleic Acids Research, 17, 3425–3433.

pYAC4 was grown and purified using standard plasmid maxi-prep protocols including caesium chloride/ethidium bromide banding (Maniatis T., Fritsch E. F., and Sambrook J., 1982, Molecular Cloning:A Laboratory Manual, Cold Spring Harbor Laboratory Press). DNA (500 μg) was digested with BamHI (200 units) and the digest was checked for completion. The salt concentration was increased, EcoRI (200 units) was added and again the digest was checked for completion. The DNA was precipitated, suspended and dephosphorylated using calf intestinal alkaline phosphatase (1 unit). The efficiency of dephosphorylation was tested by the lack of ability of the vector to self ligate to residual phosphorylated EcoRI ends.

Genomic DNA was concentrated under low vacuum (~300 mm mercury) to approximately 5 ml and then dialysed overnight in the same ultra thimble against 1 litre cold 1×TE. Dephosphorylated vector (100 μg) was added and the DNA was again concentrated to 2 ml. It was then transferred into a 15 ml sterile Falcon tube using a 1000 μl dispensing pipette with the tip cut to provide an opening of 3 mm and 220 μl of 10× ligation buffer was added. After equilibration on ice for 1 hour, T4 DNA ligase (60 units) in 800 μl 1× ligation buffer was added with gentle movement of the dispensing tip to allow gradual dispersal. After a further one hour of equilibration on ice, the ligation mix was incubated at 12° C. overnight. The ligated DNA was extracted once with phenol and once with chloroform/octanol using the gentle procedure described above and then transferred back to the same ultra thimble. The DNA was concentrated to 1.5 ml and transferred to a 1.5 ml Eppendorf tube again using a tip with an opening of 3 mm. In this state the DNA could be stored at 4° C. for several months without noticeable loss in transformation efficiency.

Saccharomyces cerevisiae AB1380 (MATa+ura3 trp1 ade2-1can1-100lys2-1his5) cells were spheroblasted with lyticase and transformed according to published protocols (P. M. J. Burgers and K. J. Percival, 1987, Analytical Biochemistry, 163, 391–397) except that less than 2 µg ligated DNA in a volume of 30 µl was used with 700 µl spheroblasts (from 17.5 ml of yeast culture). The transformation mix was plated on two 9 cm diameter plates lacking uracil and incubated at 30° C. for 48–72 hours. 100 ng uncut pYAC4 was used in a control transformation to monitor the efficiency.

Colonies were picked from within the agar onto the surface of double selection recovery plates to form an array of 96 colonies. The plates were grown at 30° C. for three days to produce large colonies. The colonies were then innoculated into 96 well microtitre plates containing 20% glycerol in SD medium. Aliquots of each colony were innoculated onto 10×10 cm plates to form a 9×96 array (864 colonies). These master plates were grown for 24 hours at 30° C. The original recovery plates were regrown at 30° C. for 2 days when the cells were harvested to make DNA plugs for PFGE and PCR analysis. Three replica lifts were taken from the master plates onto Hybond N filters and were grown overnight at 30° C. Two of the replicas were grown for a further 4 hours on SD agar containing 20% glycerol before storage at −70° C. Twelve slave lifts were taken from the third replica plate. The slave lifts were grown for 2 days at 30° C. prior to treatment with lyticase to spheroplast the cells. The cells were then lysed with 10% SDS, denatured with alkali, neutralised by washing with 2× SSC and DNA was fixed to the filters by baking or UV fixation. A total of 40 master filters was prepared (40×864 clones).

Aliquots of the glycerol stocks were used to innoculate 10 ml medium (6.7 g/L Bacto yeast nitrogen base without amino acids, 20 g/L glucose, 55 mg/L adenine, 55 mg/L tyrosine, 14 g/L casamino acids) and shaken at 400 rpm overnight at 30° C. Cells were harvested, washed once in 50 mM EDTA and resuspended to 500 µl in 1M sorbitol, 20 mM EDTA, 14 mM mercaptoethanol and 1 mg/ml Zymolase-20T. An equal volume of 1% LGT agarose in the same solution was added and the mixture was poured into a plug mould. The yeast chromosomal size marker protocol using lithium dodecyl sulphate but no protease was then followed and DNA samples were analysed on a "Waltzer" PFGE apparatus (Southern et al, 1987, Nucleic Acids Research, 15, 5925–5943).

EXAMPLE 2

Hybridisation Screening of YAC Colonies:

Master filters (in duplicate) were rinsed in 2× SSC (1× SSC is 15 mM sodium citrate, 150 mM sodium chloride). The filters were then prehybridised in 50 ml of hybridisation solution at 65° C.

Hybridisation Solution:

| | |
|---|---|
| 6.25 ml 40× Denhardts Solution | (0.8% Bovine Serum Albumin 0.8% Ficoll 400 0.8% Polyvinyl pyrrolidone) |
| 5 ml 10% SDS | |
| 2 ml 2M Na$_2$HPO$_4$ | |
| 10.5 ml 2M NaH$_2$PO$_4$ | |
| 25 ml 20% Dextran Sulphate | |

Probes were labelled with $\alpha^{32}$P dCTP to a specific activity of $10^8$–$10^9$ cpm/µg (Feinberg and Vogelstein, 1983, Analytical Biochemistry, 132, 6–13). 100 ng of probe was added to the filters in 30 ml of hybridisation solution. Hybridisation was performed at 65° C. for 16 hours in a rotating hybridisation oven (Hybaid). In an alternative procedure 50 ng of mixed probes (up to a maximum of 5) were added to the filters in 200 ml of hybridisation and hybridisation was performed at 65° C. for 16 hours in a container incubated in a water bath. The filters were then washed in 2× SSC for 30 minutes at room temperature followed by a further washes with 2× SSC (2×30 minutes at 65° C.) and a final wash with 1× SSC for 30 minutes at 65° C. Filters were air dried and exposed to X-omat AR film in cassettes at −70° C.

Filters containing positive colonies were identified and hybrisation was repeated to confirm the positive colonies. Colonies could be localised to a particular 96 well microtitre plate but individual colonies could not always be identified on the master plate because of parallax errors. A 96 prong replicating tool was used to innoculate 10 µl aliquots from the glycerol stocks in a 96 well microtitre plate to a nylon filter. Colonies were grown, spheroplasted and DNA fixed to the filter as described previously. The probes were hybridised to the filter essentially as described above but using smaller volumes and individual positive colonies were identified.

The probes used specifically hybridise to either locus A or locus B as hereinbefore defined.

PCR Screening of YAC Colonies:

DNA from YAC colonies was prepared as plugs in LGT agarose containing 864 colonies or 96 colonies. ⅓ of a plug containing ~1 µg DNA was dialysed against 1× TE for 16 hours at 4° C. The buffer was removed and replaced by 260 µl fresh 1× TE. The plug was melted at 65° C. for 5 minutes, vortexed for 1 minute and then incubated at 37° C. for 1 hour. The solution was frozen in 50 µl aliquots and stored at −20° C. Plugs containing 96 colonies were diluted to 500 µl before aliquoting.

Amplification of Locus A:

Aliquots of the plugs (2 µl) were amplified in a reaction mixture containing 10 mM Tris-HCl pH 8.3, 50 mM KCl, 1 mM MgCl$_2$, 100 µM dNTPs, 0.01% gelatin and 100 pmole of primers 1 and 2

Primer 1  CGGGTAGCCGGCTGTTATGGTATTCATTTG

Primer 2  CACCAGAATTTAGTCACTTCACATTGAGTC in a total volume of 100 µl. The reaction mixture was overlaid with 50 µl mineral oil (Sigma). Amplification with primers 1 and 2 gives a product of ~800 bp.

The reaction mixtures were incubated at 96° C. for 10 minutes in a temperature cycling machine (Techne programmable Dri-Block PHC-1). The reaction mix was cooled to 92° C., 2 units of Taq polymerase was added and amplification was performed for 38 cycles at 92° C. for 2 minutes, 63° C. for 2 minutes and 72° C. for 3 minutes. Aliquots of the reaction mixture (15 µl) were taken, dye loading mix (5 µl) was added and the samples were analysed on 1.4% agarose gels.

The predicted 800 bp product was obtained from masters Y14, Y22 and was localised to 22I.

Amplification of Locus B:

Aliquots of the plugs (2 µl) were amplified in a reaction mixture containing 10 mM Tris HCl pH 8.3, 50 mM KCl, 1 mM MgCl$_2$, 100 µM dNTPs, 0.01% gelatin and 100 pmole of primers 3 and 4

Primer 3  GTGCTATGAGTCACCTCCAGCCCACCACTG

Primer 4  TCTTCATACCTATTTTTACATCTTCCC in a total volume of 100 µl. The reaction mixture was overlaid with 50 µl mineral oil (Sigma). The reaction mixture was incubated at 96° C. for 10 minutes in a temperature cycling machine (Techne programmable Dri-Block PHC-1). The reaction mix was cooled to 92° C., 2 units of Taq polymerase was added and amplification was performed for 38 cycles at 92° C. for 2 minutes, 63° C. for 2 minutes and 72° C. for 3 minutes. Aliquots of the reaction mixture (15 µl) were taken, dye loading mix (5 µl) was added and samples were analysed on 1.4% agarose gels.

The predicted 950 bp product was obtained from masters Y14, Y34 and Y35 and the positive clones could be localised to Y14I, Y34A and Y35F.

Using the above mentioned procedures YAC clones were identified which hybridised either to locus A or to locus B. In certain clones multiple YACs are observed ie. SC/14DC12. However PFGE analysis allows fractionation of these individual YACs and subsequent identification of the YAC of interest. The YAC clones were analysed by PFGE to determine the insert size. The results are shown below:

| YAC clone | Accession Number | Size | Positive | YAC Ref No. |
|---|---|---|---|---|
| SC/14DC12 | 40204 | 500 kb | (1) | A |
| SC/35FB6 | 40209 | 340 kb | (2) | B |
| SC/22IA7 | 40202 | 300 kb | (1) | D |

EXAMPLE 3

Construction of YAC Vectorette Library:

LGH-agarose plugs containing YAC clone D (~1 µg YAC DNA per plug) were washed for 16 hours at 4° C. in 50 ml 1× TE. The plugs were divided into two parts using a sterile scalpel. The plugs were then incubated for 1 hour in 1 ml of the appropriate restriction enzyme buffer (Current Protocols in Molecular Biology, edited by Ausubel, Brent, Kingston, Moore, Smith, Seiden and Struhyl, 1987, Wiley Interscience). The solution was removed and replaced by 100 µl of fresh buffer. Plugs were digested with the following enzymes Alu 1, Hinf 1, Rsa 1, Pst 1, Sma 1, Bgl II (20 units/plug) for 2 hours at 37° C. The buffer was then removed and replaced by 100 µl 1× ligase buffer and incubated for 16 hours at 4° C.

| 1X Ligase Buffer | 20 mM Tris HCl pH7.4 |
|---|---|
| | 10 mM DTT |
| | 10 mM Mg Cl$_2$ |

The buffer was then removed and replaced by 8 µl H$_2$O and 1 µl of the appropriate ligated vectorette unit (2 pmole) and 10 µl ligase buffer. The sequence of the vectorette oligonucleotides is disclosed in UK Patent Application No 88180203 and European Patent Application, publication no. 356021. The oligonucleotides used in the construction of the Bgl II library are shown below by way of example.

(Sigma). The sequence of primers 1089, and 224 is shown below. These allow amplification of the segment of the insert from individual YAC clones adjacent to the left hand vector component. In addition, the sequences of the nested primers 1092 and 537 are given as well as primers from the amplification from the right hand vector component of YAC clones from the library. (1090, 1091)

1089 ACCCGTTCTCGGAGCACTGTCCGACCGC

224 CGAATCGTAACCGTTCGTACGAGAATCGCT

1092 AGTCCTGCTCGCTTCGCTACTTGGAGC

537 ACCGTTCGTACGAGAATCGCTGTCCTCTCC

1090 ACCTGTGGCGCCGGTGATGCCGGCCAC

1091 ATAGGCGCCAGCAACCGCACCTGTGGC

The reaction mixture was incubated at 96° C. for 10 minutes in a temperature cycling machine (Techne programmable Dri Block PHC-1). The reaction mix was cooled to 92° C., 2 units of Taq polymerase were added and amplification was performed for 35 cycles consisting of 2 minutes at 92° C., 2 minutes at 60° C. and 3 minutes at 72° C.

Aliquots (15 µl) of the reaction mixture were taken, dye loading mix (5 µl) was added and the samples were analysed on 1.4% agarose gels.

| Dye loading mix | 15% (W/V) Ficoll 400 |
|---|---|
| | 0.05% (W/V) Bromophenol Blue |
| | 0.05% (W/V) Xylene Cyanol |
| | dissolved in 1x TBE |

The results are shown in FIG. 1. Lane 1 and 2 contain a ~500 bp product of amplification of a HinfI library between primers 1089 and 224. Lanes 3 and 4 contain a ~500 bp product of amplification of a Bgl II library between primers 1089 and 224. The products were eluted for further analysis.

Figure 2:
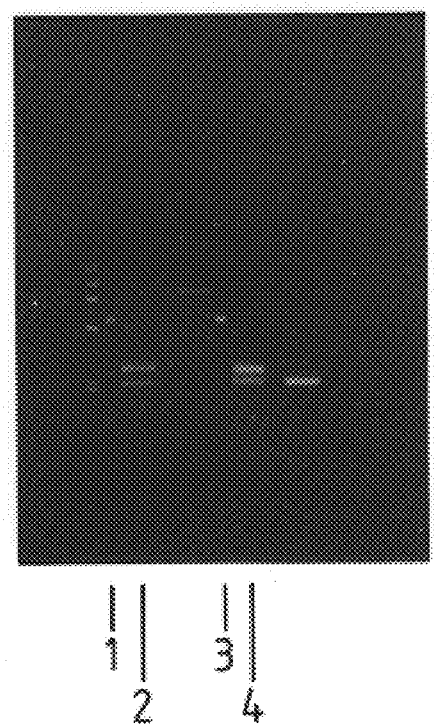
FIG. 2 shows in lane 1 a purified HinfI product from FIG. 1. Lane 2 shows an EcoRI digestion product of the HinfI product. Lane 3 shows a purified Bgl II product. Lane 4 shows the product of EcoRI digestion of the Bgl II product.
Figure 3:
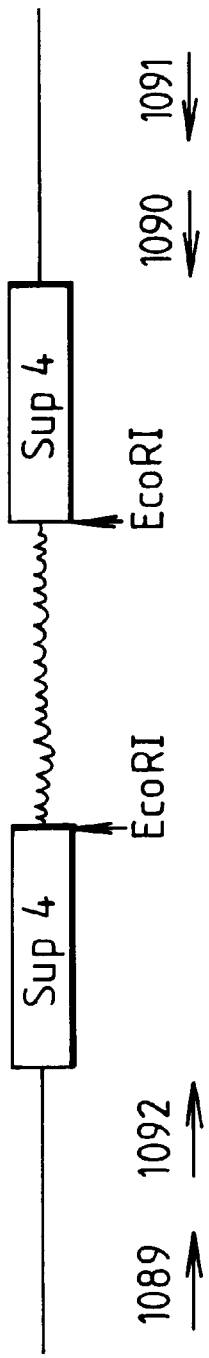
FIG. 3 shows the relative positions of primers 1089, 1090, 1091, 1092, the sup 4 vector sequences and the YAC insert as well as the EcoRI cloning sites.
Figure 6:
FIG. 6 shows the defined 3' and 5' directions with respect to the KM19 and J3.11 markers.

The products were digested with EcoRI to remove the Sup 4 sequences. In FIG. 2, lane 1 shows the purified HinfI product, lane 2 shows the products of EcoRI digestion of the HinfI product, lane 3 shows the purified Bgl II product. Lane 4 shows the products of EcoRI digestion of the Bgl II product. In lanes 2 and 4, the lower product represents the Sup 4 sequences while the upper product represents the terminus of the YAC insert.

The HinfI and Bgl II products were eluted and sequenced using primer 368 CGCTGTCCTCTCCTT as described by Newton et al, 1988, Nucleic Acids Research, 16, 8233–8243.

The right hand terminus of YAC D was amplified in a reaction containing 10 mM Tris HCl pH 8.3, 50 mM KCl, 1

```
5'GATCGAAGGAGAGGACGCTGTCTGTCGAAGGTAAGGAACGGAGGAGAGAAGGGAGAG 3'

3'    CTTCCTCTCCTGTCGCTAAGAGCATGCTTGCCAATGCTAAGCTCTTCCCTCTC 5'
```

The agarose was melted at 65° C. for 15 minutes and allowed to cool at 37° C. 10 mM ATP (1 µl) and T4 DNA ligase (1 µl, 9 units) was added and ligation performed at 37° C. for 1 hour. The reaction was incubated at 65° C. for 15 minutes and then stored frozen at −20° C.

Amplification of YAC Vectorette Libraries 10 ng of each library was amplified in a reaction mix containing 10 mM Tris HCl pH 8.3, 50 mM KCl, 1 mM MgCl$_2$, 100 µM dNTPs and 0.01% gelatine and 100 pmole primers 1089 and 224 in a final volume of 100 µl. The reaction mixture was overlaid with 50 µl mineral oil mM MgCl$_2$, 100 µM dNTPs and 0.01% gelatine and 100 pmole primers 1090 and 224 in a final volume of 100 µl. The reaction mixture was overlaid with 50 µl mineral oil (Sigma).

The reaction mixture was incubated at 96° C. for 10 minutes in a temperature cycling machine (Techne Programmable Dri Block PHC-1). The reaction mix was cooled to 92° C., 2 units of Taq polymerase were added and amplification was performed for 35 cycles consisting of 2 minutes at 92° C., 2 minutes at 60° C. and 3 minutes at 72° C. Aliquots of the reaction mixture (15 µl) were taken, dye loading mix (5 μl) was added and the samples analysed on 1.5% agarose gels.

A 650 bp product was obtained by amplification of a Rsa 1 library and a 450 bp product was obtained by amplification of an Alu 1 library. Digestion of the products with EcoRI releases the predicted products of 500 bp (Rsa 1) and 300 bp (Alu 1) respectively (Lanes 3 and 4). Both products were eluted and sequenced with primer 368. The sequences of the left and right hand termini of YAC D are as follows:

Left Hand Terminal Sequence:

```
EcoRI

GAATTCTATA AACTGTATTA ATATTAATAA TCTGTCTCTG AGATATTGTG ATAAAAACAA    60

CTTTGATTTT GCACATAAAA ATGTAGGGTA AATAATAAAA TGAAGGTTAG TAAGCTTCTA   120

TGTCTAATTT ATCACTGTTG TAGATAATCT CAATTAATTT GATTACATCC ATAGTCCTTG   180

ACATGTTATA GTTTTTCATG TCCTTGTTAG TGAAGTTTCA TCTATGCAAA GTAATTTTAA   240

GGGTACCCTA TAATCTCAGG GTGTATGAGA AATATTACTC TTTAA                   305
```

Right Hand Terminal Sequence:

```
AGGCCAGGAN GATGGCTCAT GCTGTAATCC CAGCASTTTG GGAGGCCAAG GCAGGCAATC    60

ACTCGAGGAG TTCAAGACCA GCCTAGCCAA CATGATNAAA CCCTNTNTAC TAAAAATACA   120

AAAATTAGCT GGGTTTGG                                                 138
```

The left hand and right hand vectorette derived sequences from the respective termini of the YAC insert can be used as described hereinbefore to rescreen the YAC library to obtain additional overlapping clones.

Using procedures directly analogous to those described above, vectorette libraries were prepared from YAC A (SC/14DC12) excised from a PFGE gel to ensure isolation of insert-termini only from this YAC. In certain clones multiple YACs are observed, however PFGE analysis allows fractionation of these individual YACs and subsequent identification of the YAC of interest. Insert-terminal vectorette PCR products were successfully isolated from both ends of YAC A. These were treated with EcoRI to remove the vector sequences and used for hybridisation with mapping filters prepared from YAC A to ensure that only fragments corresponding to YAC A were detected. PCR primer pairs specifying both ends of YAC A were synthesised. The sequences of the left and right hand termini of YAC A are as follows:

Left Hand Terminal Sequence:

```
AAGCAAGTTA TTGTGTTATG CACTCTATAA GGGACAGAAA ACTTAGTAAG AAAAAATCTG    60

TTTTATCTAG CATTTCTATT ACATTCTTTA TCTAGCCTGC TTTAATTGGT GATGATTTTG   120

TGTTTAAACC TTGCTTTCTT AACTAGGATA CCTGCAAGTA TTTACAATGC TAAGTGGAAA   180

TTA AA                                                              185
```

Right Hand Terminal Sequence:

```
TGACTTGGCT CAGGCCTGTA TCATTTACAG TAGAAATATA ATGNNGYGGC TGCTGAAGTT    60

ACTGTTCTTG AGGGTTGAGC TGCAGCCACT GAAGATTGTN GAAAAACATG CCTCTTGTTT   120

CTCACCCCAT ATCATGAAAT GGGTTCTTTC AAGTTTATTC CCTGCTGCTT TTCCTGGAGA   180

CGTCTACTGA GTTGCTGGT                                                199
```

Orientation of YAC A was achieved by hybridisation with probes for the the probe (1) locus as herein before described, and comparison of the restriction map with genomic PFGE maps. These indicated that YAC A extended ~350 kb from KM19 towards J3.11. The library was then rescreened with PCR primers for the left hand end of the YAC A insert. The screening procedure identified YAC C.

| YAC clone | Accession Number | Size | Positive | YAC Ref No. |
|---|---|---|---|---|
| SC37AB12 | 40302 | 310 kb | (1) | C |

Using procedures analogous to those outlined above the left hand terminal sequence of YAC C was sequenced:

CTGGATTTGC TCATATACTC TTGTTCTTCT TACACTCAAA GCACTTCTGA ATGGAAATTA 60

TTTAGTAACA AGGACAAAGA TGGATTTCAT GAACTA 96

EXAMPLE 4

Identification of Transcripts/Coding Sequences Using YACs:

A) Northern Blotting:

Total RNAs in a buffer solution containing 50% formamide and 2.2M formaldehyde were heated to 70° C. for 10 minutes, chilled on ice, and electrophoretically fractionated on 1% agarose-formaldehyde gels prior to Northern blotting onto Hybond N membranes (Amersham) according to the manufacturers instructions.

Hybridisation conditions:

Hybond N filters from either Northern or Southern blots were prehybridised in a buffer containing 3× SSC, 5× Denhardts (0.1% Ficoll 400 (Pharmacia), 0.1% polyvinylpyrrolidone mol. wt. 360 k, 0.1% bovine serum albumin), 200 μg/ml salmon sperm DNA, 0.1% SDS, 6% polyethylene glycol 6000, for at least 6 hours at 65° C. Hybridisations were performed in a buffer containing 5× SSC, 5× Denhardts, 200 μg/ml salmon sperm DNA, 0.1% SDS, 6% polyethylene glycol 6000, for at least 16 hours at 65° C. with a probe concentration of ~8 ng/ml and a specific activity of $1.7 \times 10^9$/μg. Following hybridisation, filters were washed at 65° C. in 2× SSC, 0.1% SDS for 20 minutes and then in 0.5× SSC, 0.1% SDS for 20 minutes. The filters were exposed to Kodak X-omat AR film with intensifying screens at −70° C.

Probe Preparation:

YAC D and YAC A (~150 ng in low melting point agarose) were $\alpha^{32}$P labelled with 300 μCi $\alpha^{32}$P dCTP for 18 hours by the method of Feinberg and Vogelstein (Analytical Biochemistry, 1983, 132, 6–13; ibid 137, 266–267). Agarose was removed by phenol/chloroform extraction and the labeled DNAs were precipitated with ammonium acetate and absolute ethanol for 10 minutes at room temperature in the presence of 100 μg sheared human placental DNA. The labelled YACs were allowed to undergo reassociation to Cot 250 in the presence of sheared human placental DNA at 65° C. for 2.5 hours prior to hybridisation to the filters.

Probing of Northern Blots:

RNA was prepared from cell line 408 (normal adult fibroblast), cell lines 4541 and 4322 (fibroblast cell lines established from two CF patients), cell line 6167 (foetal fibroblasts), cell line BxPC (pancreatic adenocarcinoma) and analysed by Northern blotting as described above. The lanes shown in FIGS. 4 and 8a below are as follows:

| Lane 1 | 408 fibroblasts |
| Lane 2 | 4541 fibroblasts |
| Lane 3 | 4322 fibroblasts |
| Lane 4 | 6167 foetal fibroblasts |
| Lane 5 | BxPc pancreatic adenocarcinoma |
| Lane 6 | small intestine |

YAC D

Figure 4:
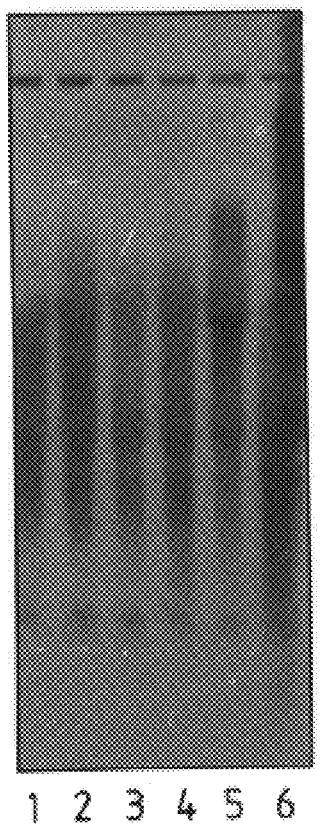
FIG. 4 shows Northern Blots probed with labelled YAC D. Lane 1 shows 408 fibroblasts, lane 2 shows 4541 fibroblasts, lane 3 shows 4322 fibroblasts, lane 4 shows 6167 foetal fibroblasts, lane 5 shows BxPc pancreatic adenocarcinoma and lane 6 shows small intestine.

FIG. 4: a strongly hybridising band of approximately 5–6 kb was observed in the lane containing RNA from the adenocarcinoma cell line. The same product was also visible in the other lanes.

YAC A

Figure 8A:
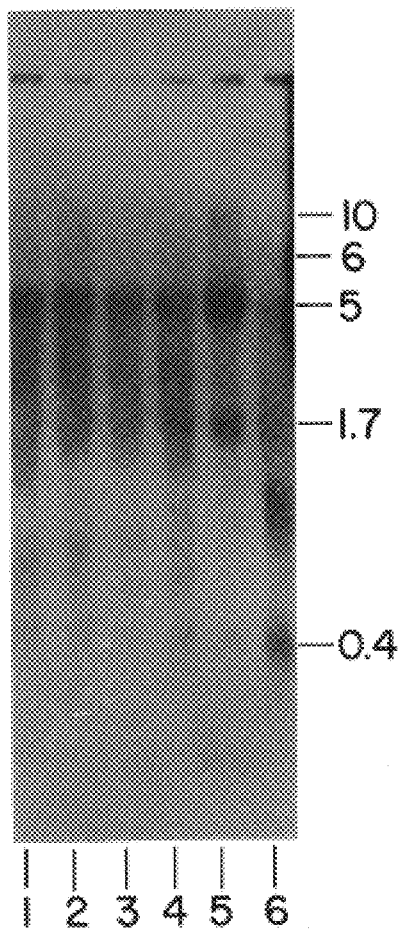
FIG. 8a shows Northern Blots probed with labelled YAC A. Lane 1 shows 408 fibroblasts, lane 2 shows 4541 fibroblasts, lane shows 4322 fibroblasts, lane 4 shows 6167 foetal fibroblasts, lane 5 shows BxPc pancreatic adenocarcinoma and lane 6 shows small intestine.

FIG. 8a: bands are visible at ~6 kb in lanes 4 and 5 which may correspond to a CF transcript. Lane 5 also shows a strong signal of ~10 kb. All lane show signals at ~5, ~1.7 and ~0.4 kilobases. The signal at ~5 kilobases may represent ribosomal RNAs.

B) cDNA Screening

YACs can be used directly as hybridisation probes to screen cDNA libraries for the identification of coding sequences. In general, $2 \times 10^4$ to $10^5$ recombinant cDNA clones were screened with each radiolabelled YAC. cDNA clones were then plated onto E. coli host strain using LB agar plates, grown overnight at 37° C. and two replica filters made on Hybond-N (Amersham International). DNA was fixed onto the filter as per the manufacturers instructions and the filters hybridised to the $^{32}$P radiolabelled YAC. Following overnight hybridisation, filters were washed down to 0.5× SSC and autoradiographed on X-omat AR film (Kodak) at −70° C. Plaques identified as duplicate positive in this first round of screening were removed from the agar plate using sterile pasteur pipettes and transferred to 200 ul SM containing 1 ul chloroform for storage at 4° C. (SM=0.58% NaCl, 0.2% MgSO$_4$. 7H$_2$O, 0.01% gelatin and 50 mM Tris.HCl pH7.5). The titre of these phage stocks was determined and they were replated at approximately 100 plaques per 9 cm diameter agar plate. Duplicate plaque lifts were made as described above and these filters were rescreened with the YAC probe. Duplicate positive cDNA clones were identified and picked into 200 ul SM. These clones were used as hybridisation probes to localise them to the YAC used to screen the cDNA library. They can also be used to obtain sequence information from the coding region of the gene(s) with the YAC.

Figure 8B:
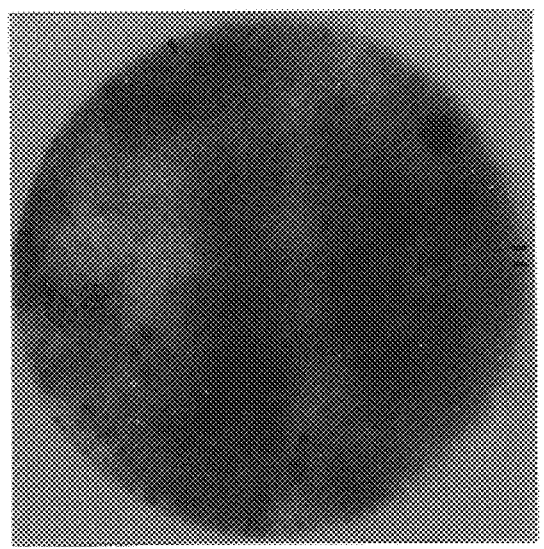
FIG. 8b shows a representative filter from a foetal liver cDNA library hybridised with YAC A. The signals bounded by dotted lines were found also on duplicate filters.

FIG. 8b: this is a representative filter from a foetal liver cDNA library hybridised with YAC A. The signals bounded by the dotted lines indicated on the filter were also found on duplicate filters.

EXAMPLE 5

Detection of Polymorphisms Using YACs:

Probe preparation and hybridisation conditions were identical to those given in Example 4 above.

Southern Blotting:

After digestion with various restriction enzymes, human genomic DNA (5 μg/lane) was electrophoretically fractionated on 1% agarose gels and then transferred to Hybond N membranes (Amersham) according to the manufacturers instructions.

Probing of Southern Blots:

DNA was prepared from 20 individuals affected by CF and from 20 normal individuals. The CF individuals had been genotyped with known markers and shown to possess the most common haplotype associated with CF in Northern Europeans. The DNAs were digested with the following enzymes MspI, TaqI, RsaI, PstI, BglI. Equal aliquots from each sample were then pooled to give a total of 10 μg/lane. Southern blots and probing was performed as described above. The results are shown in FIG. 5:

| | |
|---|---|
| Lane 1 | pooled CF DNA, Bgl II digest, probed with YAC D |
| Lane 2 | pooled normal DNA, Bgl II digest, probed with YAC D |
| Lane 3 | hydatidiform mole DNA, Bgl II digest, probed with YAC D |
| Lane 4 | hydatidiform mole DNA, Bgl II digest, probed with YAC D |
| Lane 5 | YAC D DNA, Bgl II digest, probed with YAC D |

A polymorphism can be detected by comparison of the lanes containing the CF and normal DNAs. A band of about 14 kb which is present in normal individuals is missing in CF patients.

Figure 5:
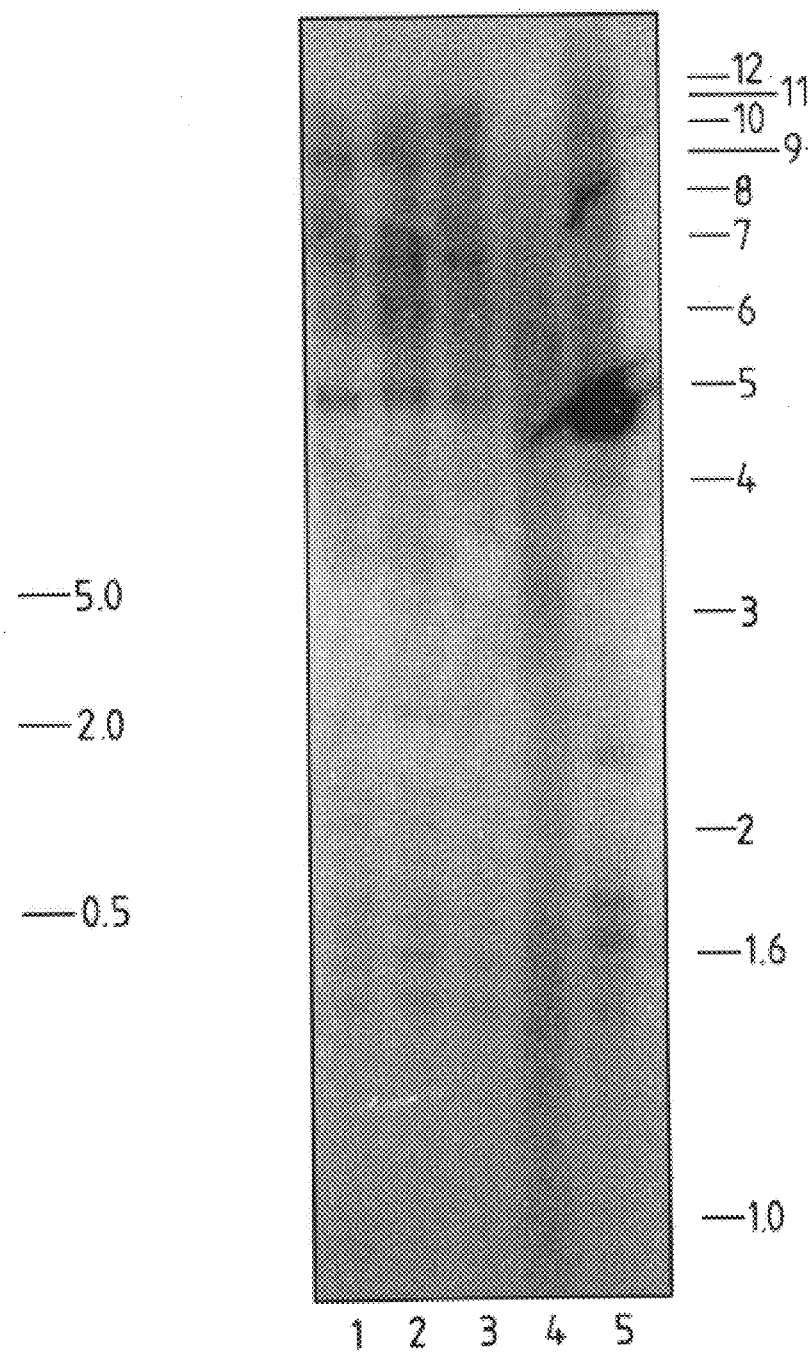
FIG. 5 shows Southern Blots probed with labelled YAC D. Lane 1 shows pooled CF DNA, Bgl II digest probed with YAC D; lane 2 shows pooled normal DNA, Bgl II digest probed with YAC D; lane 3 shows hydatidiform mole DNA, Bgl II digest probed with YAC D; lane 4 the same and lane 5 shows YAC D DNA, Bgl II digest, probed with labelled YAC D.
Figure 7:
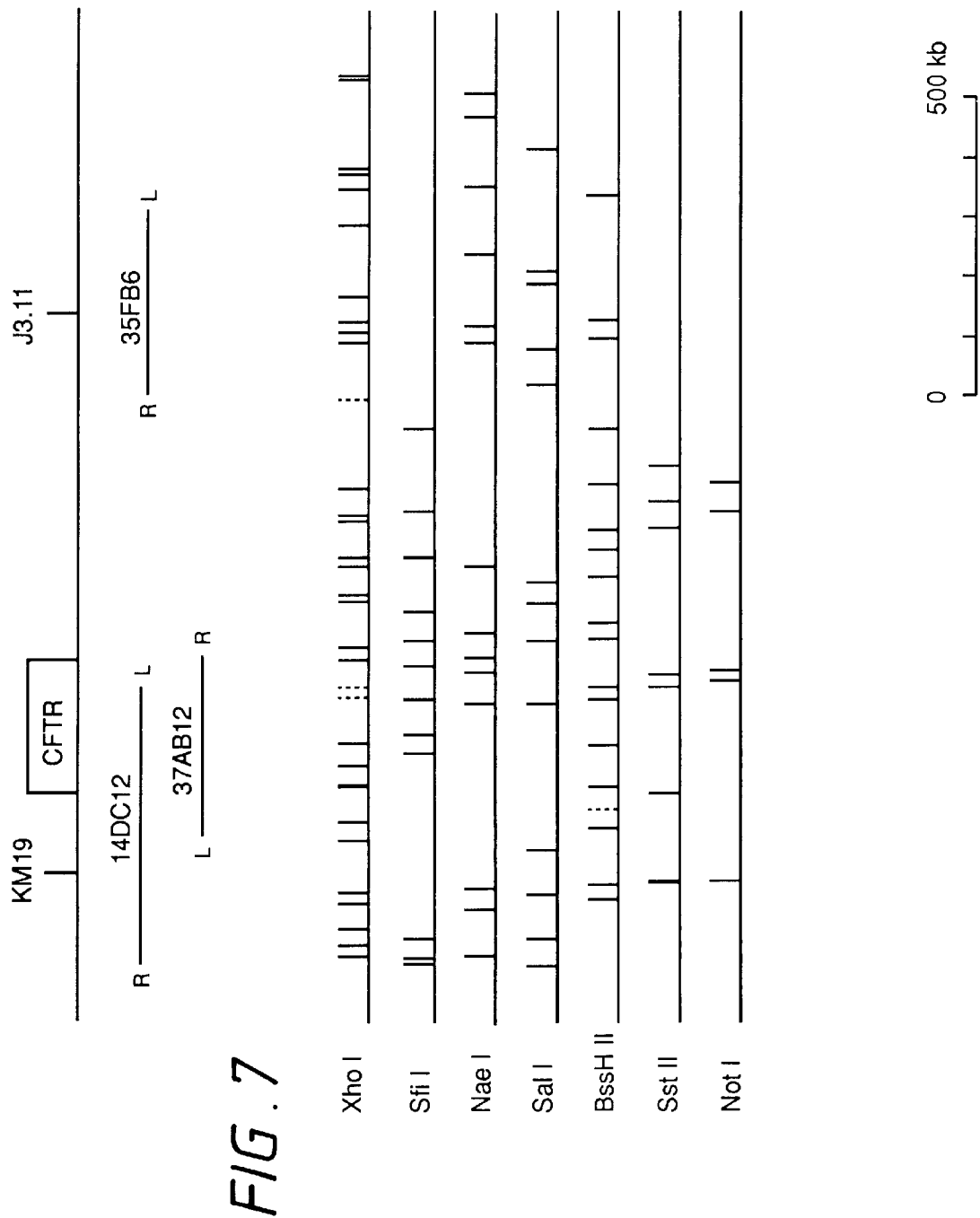
FIG. 7 shows the position of the cystic fibrosis gene (CFTR) in relation to the KM19 and J3.11 loci and YACs of the present invention. Also shown is the restriction map for the restriction enzymes Xho I, Sfi I, Nae I, Sal I, Bssh II, Sst II and Not I.

In FIG. 5 it can be seen that the pattern observed in lane 2 with normal DNA is identical to that observed in lane 5 which contains YAC D Bgl II digested DNA. This observation confirms that the human DNA cloned into YAC D is an authentic and faithful copy of normal human genomic DNA at this locus and shows that the human DNA in YAC D is not rearranged.

In the following sequence listing, sequence identities 23–30 correspond to convenient pairs of primers for the following loci: KM19, J3.11 and the right and left hand terminal sequences of YAC A respectively. All sequences are read 5'–3'.

What is claimed is:

1. Yeast artificial chromosome SC/14DC12.
2. Yeast artificial chromosome SC/35FB6.
3. Yeast artificial chromosome SC/37AB12.
4. A yeast artificial chromosome comprising an insert containing a cystic fibrosis gene, wherein the insert is a nucleotide sequence of 300 kilobases to about 500 kilobases.
5. The yeast artificial chromosome of claim 4, wherein the cystic fibrosis gene is from an individual not affected by cystic fibrosis.
6. A method of detecting or distinguishing cystic fibrosis comprising:

preparing a sample of nucleic acid from an individual; and detecting the presence of a cystic fibrosis gene in said sample by hybridization to a yeast artificial chromosome according to claim 4.

7. A method of detecting transcripts or genomic DNA coding sequences for a cystic fibrosis gene which hybridize to a yeast artificial chromosome comprising:

preparing a sample of nucleic acid; and detecting said transcripts or genomic DNA coding sequences by hybridization to a yeast artificial chromosome according to claim 4 as a hybridization probe.

* * * * *

SEQUENCE LISTING (1) GENERAL INFORMATION:

(iii) NUMBER OF SEQUENCES: 30

(2) INFORMATION FOR SEQ ID NO:1:

(i) SEQUENCE CHARACTERISTICS:
      (A) LENGTH: 150 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

CGGGTAGCCG GCTGTTATGG TATTCATTTG ATCTAGCCCT AATGTAATCT TGTCAACCAG    60

GTGGTCTTTT CCTTTTGCTT CAAATAGACT TTAGGTGCTC TTAAAATTTT CAGCATCCTA   120

TAGTACTAAC CTAAATTTTC AGCATCCTAT    150

(2) INFORMATION FOR SEQ ID NO:2:

(i) SEQUENCE CHARACTERISTICS:
      (A) LENGTH: 100 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:2:

GACTCAATGT GAAGTGACTA AATTCTGGTG AGTATGGCTG AGAGGTTGAG GATCTCTCCT    60

TTCACTGAGC ACCATAGGAT GAGANNNNTT CTCCCAGACA    100

(2) INFORMATION FOR SEQ ID NO:3:

(i) SEQUENCE CHARACTERISTICS:
      (A) LENGTH: 142 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:3:

GTGCTATGAG TCACCTCCAG CCCACCACTG TTTGAATGGT ATTTAAAGTG AAGGTACAGA        60

AGCTATTTWA AAGGTCACAG AAGTAACCTA GGCAAGTGAT AAAGAGACTA AATTAAGGTA       120

GCAGAAATAG GAGAGACTAT TT                                               142

(2) INFORMATION FOR SEQ ID NO:4:

(i) SEQUENCE CHARACTERISTICS:
        (A) LENGTH: 180 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

ATGCCTGCAG GTCGACTCTA GAGGATYCCC CTAGAGCATA TAAAATTATT TTCAAGGGAA        60

GATGTAAAAA TAGGTATGAA GAAGTTCTGG TACTTTTTTC CCCACCCAGC AGATCACTGT       120

TTTTTTTTTT TTNTTTTTTT TTTTTTTTTT TATCACTTGA GTGTTATGCA CTGCTCTTTA       180

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

CGGGTAGCCG GCTGTTATGG TATTCATTTG                                        30

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

CACCAGAATT TAGTCACTTC ACATTGAGTC                                        30

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

GTGCTATGAG TCACCTCCAG CCCACCACTG                                        30

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

TCTTCATACC TATTTTTACA TCTTCCC                                               27

(2) INFORMATION FOR SEQ ID NO:9:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

GATCGAAGGA GAGGACGCTG TCTGTCGAAG GTAAGGAACG GAGGAGAGAA GGGAGAG              57

(2) INFORMATION FOR SEQ ID NO:10:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

CTCTCCCTTC TCGAATCGTA ACCGTTCGTA CGAGAATCGC TGTCCTCTCC TTC                  53

(2) INFORMATION FOR SEQ ID NO:11:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

ACCCGTTCTC GGAGCACTGT CCGACCGC                                              28

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

CGAATCGTAA CCGTTCGTAC GAGAATCGCT                                            30

(2) INFORMATION FOR SEQ ID NO:13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

```
AGTCCTGCTC GCTTCGCTAC TTGGAGC                                                    27

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

ACCGTTCGTA CGAGAATCGC TGTCCTCTCC                                                 30

(2) INFORMATION FOR SEQ ID NO:15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

ACCTGTGGCG CCGGTGATGC CGGCCAC                                                    27

(2) INFORMATION FOR SEQ ID NO:16:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

ATAGGCGCCA GCAACCGCAC CTGTGGC                                                    27

(2) INFORMATION FOR SEQ ID NO:17:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

CGCTGTCCTC TCCTT                                                                 15

(2) INFORMATION FOR SEQ ID NO:18:

(i) SEQUENCE CHARACTERISTICS:
        (A) LENGTH: 285 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

GAATTCTATA AACTGTATTA ATATTAATAA TCTGTCTCTG AGATATTGTG ATAAAAACAA        60

CTTTGATTTT GCACATAAAA ATGTAGGGTA AATAATAAAA TGAAGGTTAG TAAGCTTCTA       120

TGTCTAATTT ATCACTGTTG TAGATAATCT CAATTAATTT GATTACATCC ATAGTCCTTG       180
```

```
ACATGTTATA GTTTTTCATG TCCTTGTTAG TGAAGTTTCA TCTATGCAAA GTAATTTTAA        240

GGGTACCCTA TAATCTCAGG GTGTATGAGA AATATTACTC TTTAA                       285
```

(2) INFORMATION FOR SEQ ID NO:19:

(i) SEQUENCE CHARACTERISTICS:
        (A) LENGTH: 138 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

```
AGGCCAGGAN GATGGCTCAT GCTGTAATCC CAGCASTTTG GGAGGCCAAG GCAGGCAATC        60

ACTCGAGGAG TTCAAGACCA GCCTAGCCAA CATGATNAAA CCCTNTNTAC TAAAAATACA       120

AAAATTAGCT GGGTTTGG                                                     138
```

(2) INFORMATION FOR SEQ ID NO:20:

(i) SEQUENCE CHARACTERISTICS:
        (A) LENGTH: 185 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

```
AAGCAAGTTA TTGTGTTATG CACTCTATAA GGGACAGAAA ACTTAGTAAG AAAAAATCTG        60

TTTTATCTAG CATTTCTATT ACATTCTTTA TCTAGCCTGC TTTAATTGGT GATGATTTTG       120

TGTTTAAACC TTGCTTTCTT AACTAGGATA CCTGCAAGTA TTTACAATGC TAAGTGGAAA       180

TTAAA                                                                   185
```

(2) INFORMATION FOR SEQ ID NO:21:

(i) SEQUENCE CHARACTERISTICS:
        (A) LENGTH: 199 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

```
TGACTTGGCT CAGGCCTGTA TCATTTACAG TAGAAATATA ATGNNGYGGC TGCTGAAGTT        60

ACTGTTCTTG AGGGTTGAGC TGCAGCCACT GAAGATTGTN GAAAACATG CCTCTTGTTT        120

CTCACCCCAT ATCATGAAAT GGGTTCTTTC AAGTTTATTC CCTGCTGCTT TTCCTGGAGA       180

CGTCTACTGA GTTGCTGGT                                                    199
```

(2) INFORMATION FOR SEQ ID NO:22:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

```
CTGGATTTGC TCATATACTC TTGTTCTTCT TACACTCAAA GCACTTCTGA ATGGAAATTA        60
```

TTTAGTAACA AGGACAAAGA TGGATTTCAT GAACTA                                96

(2) INFORMATION FOR SEQ ID NO:23:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

GCTAATATGT GCAGCCAAAT CACTA                                           25

(2) INFORMATION FOR SEQ ID NO:24:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

GCTAGTTCAA ACTGACTGTT GAGCC                                           25

(2) INFORMATION FOR SEQ ID NO:25:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

AAGTTTGAGC ATAGGAAAAG TTCTGTGCCC                                      30

(2) INFORMATION FOR SEQ ID NO:26:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

CATCCTTGAC TCTTCTCTTT CTCAAAGGCC                                      30

(2) INFORMATION FOR SEQ ID NO:27:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

TGGCTCAGGC CTGTATCATT TACAG                                           25

(2) INFORMATION FOR SEQ ID NO:28:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:28:

ACCAGCAACT CAGTAGACGT CTCC                                      24

(2) INFORMATION FOR SEQ ID NO:29:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

ATATCTTATC TTAGAGTAAT CCTTG                                     25

(2) INFORMATION FOR SEQ ID NO:30:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

AAGCAAGTTA TTGTGTTATG CACTC                                     25